United States Patent [19]

Trivedi et al.

[11] Patent Number: 4,862,359
[45] Date of Patent: Aug. 29, 1989

[54] TOPOGRAPHICAL MAPPING OF BRAIN FUNCTIONALITY FROM NEUROPSYCHOLOGICAL TEST RESULTS

[75] Inventors: Sushma S. Trivedi, Sunnyale, Calif.; Raquel E. Gur; Ruben Gur, both of Philadelphia, Pa.

[73] Assignee: Bio-Logic Systems Corporation, Mundelein, Ill.

[21] Appl. No.: 947,673

[22] Filed: Dec. 30, 1986

Related U.S. Application Data

[63] Continuation-in-part of Ser. No. 646,614, Aug. 31, 1984, Pat. No. 4,744,029.

[51] Int. Cl.$^4$ .......................... A61B 5/04; G06F 15/42
[52] U.S. Cl. ............................... 364/413.05; 128/731
[58] Field of Search ........... 364/413, 415, 417, 413.05; 128/731; 367/70

[56] References Cited

U.S. PATENT DOCUMENTS 4,407,299 10/1983 Culver ................................. 128/731
4,408,616 10/1983 Duffy et al. ......................... 128/731
4,421,122 12/1983 Duffy .................................. 128/731

OTHER PUBLICATIONS

Nagata, K. et al., "Topographic Electroencephalographic Study of Transient Ischemic Attacks," *Electroencephalography and Clinical Neurophysiology*, vol. 58, No. 4, Oct. 1984, 291–301.
Celesia, G. G. et al., "Visual Evoked Potentials and Positron Emission Tomographic Mapping of Regional Cerebral Blood Flow and Cerebral Metabolism: Can the Neuronal Potential Generators be Visualized?", *Electroencephalography and Clinical Neurophysiology*, vol. 54, No. 3, Sep. 1982, 243'256.
BEAM brochure, Braintech Inc., date unknown.
Duffy, F. H., "Brain Electrical Activity Mapping (BEAM): Computerized Access to Complex Brain Function", *Intern. J. Neuroscience*, vol. 13, 1981, 55–65.
Duffy, F. H. et al., "Age-Related Differences in Brain Electrical Activity of Healthy Subjects", *Compilation of Technical Articles Concerning the BEAM Method*, date unknown, 1–36.
Matsuda, H. et al., "Age-Matched Normal Values and Topographic Maps for Regional Cerebral Blood Flow Measurements by Xe-133 Inhalation," *Stroke*, vol. 15, No. 2, Mar.-Apr. 1984, 336–342.
Wilkus, R. J. et al., "Neuropsychological Correlates of the Electroencephalogram in Epileptics: I. Topographic Distribution and Average Rate of Epileptiform Activity", *Epilepsia*, vol. 17, No. 1, Mar. 1976, 89–100.
Duffy, F. H. et al., "Brain Electrical Activity in Patients with Presenile and Senile Dementia of the Alzheimer Type", *Annals of Neurology*, vol. 16, No. 4, Oct. 1984, 439–448.
Katayama, Y. et al., "Changes in Regional Cerebral Blood Flow and Oxygen Metabolism Following Ventrolateral Thalamotomy in Parkinson Syndrome as Revealed by Positron Emission Tomography", *Appl. Neurophysiol.*, vol. 49, 1986, 76–85.
Nagata, K. et al., "Topographic Electroencephalographic Study of Cerebral Infarction Using Computed Mapping of EEG", *J. Cereb. Blood Flow Metab.*, vol. 2, No. 1, 1982, 79'88.

*Primary Examiner*—Clark A. Jablon
*Attorney, Agent, or Firm*—Niro, Scavone, Haller & Niro, Ltd.

[57] ABSTRACT

A method and apparatus for evaluating physiological and behavioral functioning of predetermined regions of interest of the human brain by displaying topographical maps of measured information. Brain electrical activity and/or predetermined physical parameters are measured in association with selected neuropsychological tests, and the measured information is operated on by providing weighted output signals characteristic of physiological functioning of the regions of interest of the patient's brain. The resulting weighted output signals are plotted as a topographical map. The measured brain electrical activity and measured predetermined physical parameters are also compared and a conversion matrix developed based on data bases of measured information for normal and abnormal subjects.

43 Claims, 13 Drawing Sheets

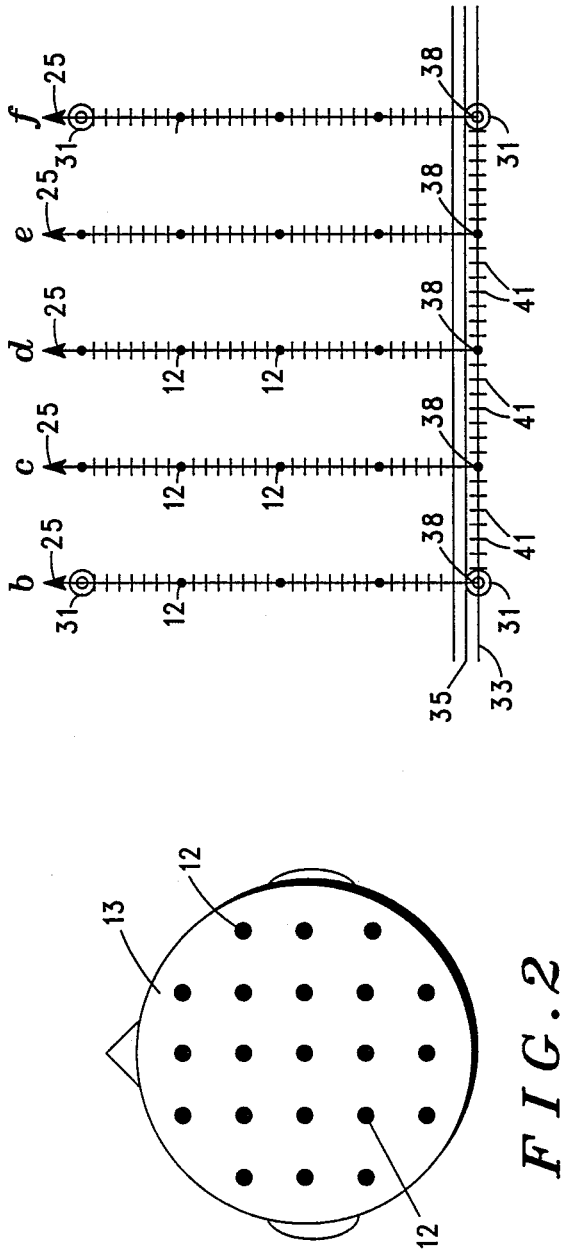
FIG. 3
FIG. 2
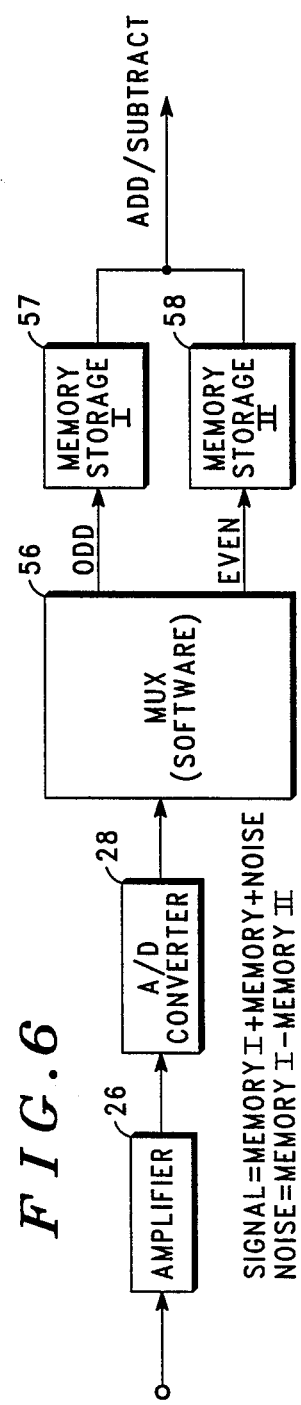
FIG. 6
SIGNAL = MEMORY I + MEMORY + NOISE
NOISE = MEMORY I − MEMORY II

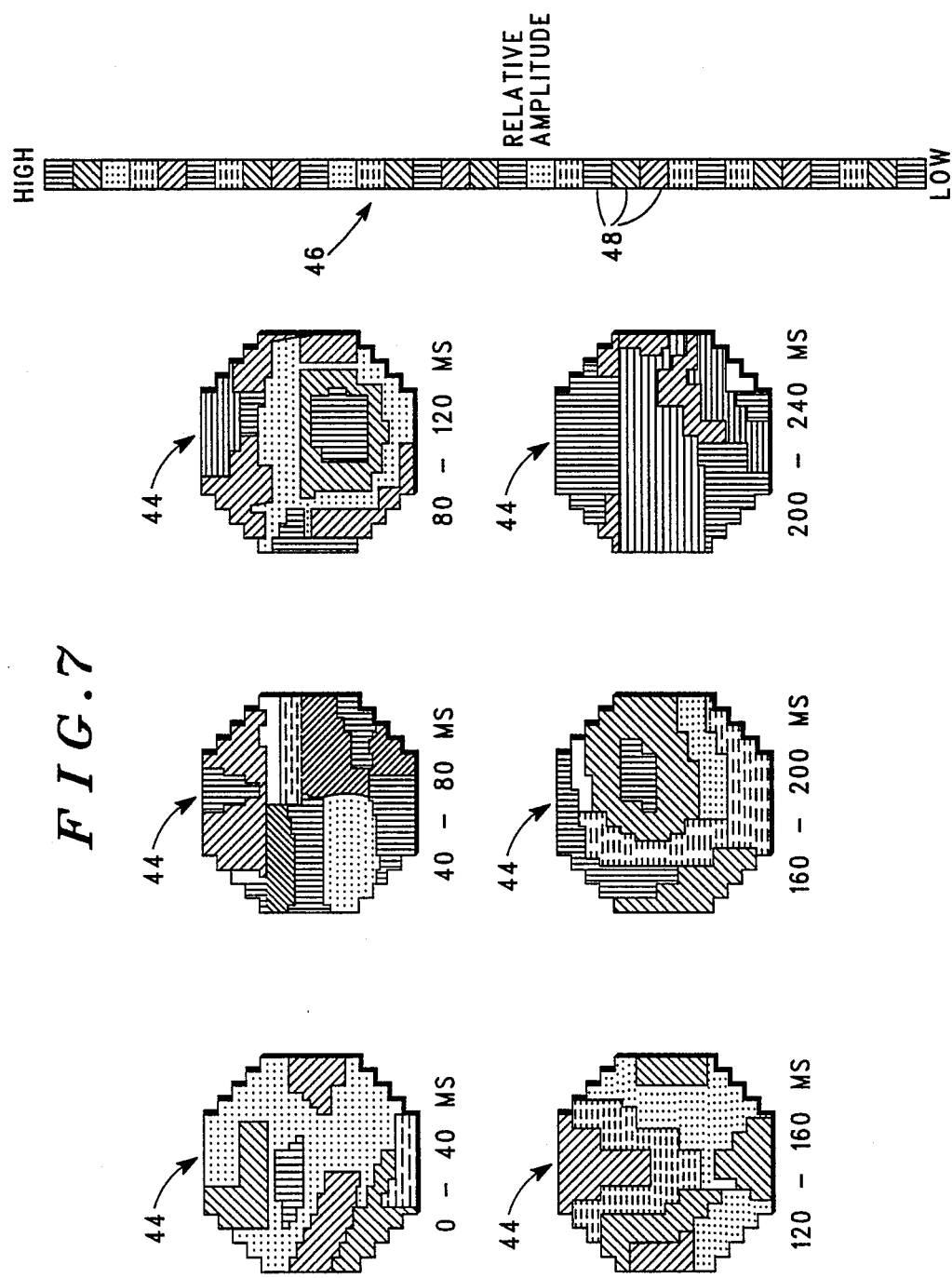

TOPOGRAPHICAL MAPPING OF BRAIN FUNCTIONALITY FROM NEUROPSYCHOLOGICAL TEST RESULTS

This application is a continuation in part of a previous application filed, Aug. 31, 1984, having Ser. No. 646,614, now Pat. No. 4,744,029.

The present inventions relate generally to an apparatus and method for displaying a topographical map of brain characteristics of a patient. More particularly the inventions relate to a novel method and apparatus for evaluating physiological functions and behavioral patterns of a patient's brain. Computer software is used for processing measured test information from a patient, and the processed test information is output in the form of various topographical maps which provide functional information characteristic of a patient's brain.

Information on neurophysiological processes in conscious patients can be obtained by, for example, x-ray computerized tomography ("XCT," hereinafter) and nuclear magnetic resonance ("NMR," hereinafter) for anatomical information and positron emission tomography ("PET," hereinafter), regional cerebral blood flow ("rCBF," hereinafter), and measurement of evoked electrical and magnetic activity and magnetoencephelogram electroencephelogram measurements ("EEG," hereinafter) for physiological information. Such measurements often yield a complicated information, such as, for example, EEG time varying outputs. A detailed and thorough analysis of complicated EEG information requires computer manipulation to determine differences of brain electrical activity of a patient compared to a normal population. A number of limitations currently exist for computer manipulation and analysis of all brain measurement.

Each particular brain analysis technique provides selected information on different aspects of regional brain function, and each technique has its inherent advantages and limitations. For example, although the XCT method provides excellent spatial resolution and bone to soft tissue contrast, the XCT method has poor soft tissue contrast for gray and white matter imaging. The XCT method also provides virtually no information on the physiology of the brain. The PET method provides images which primarily depict physiological activity of the patient. Integration of anatomical and physiological information has not generally been achieved by these techniques.

There are methods of reconstructing three dimentional images from tomographic information both for anatomical information obtained in XCT methods and for physiological information obtained by PET or single photon emission computed tomography ("SPECT," hereinafter). These methods do not apply to non-tomographic techniques, such as, the isotope clearance method for measuring rCBF or the measurements of the electrical potential (such as EEG measurements) and magnetic potentials on the scalp. The clinical utility of EEG is fairly well established, and techniques to generate topographic maps from the EEG data have been developed (see, for example, U.S. Pat. No. 4,408,616, which is incorporated by reference herein).

Studies in the recent past have indicated that the measurements of the rCBF may be informative in assessing brain function in normal subjects, as well as in patients with neurologic and psychiatric disorders. Several brain techniques such as nitrous oxide inhalation (see, for example, S. D. Kety, R. B. Woodford, M. M. Hamel et al., Cerebral blood flow and metabolism in schizophrenia, *American Journal of Psychiatry*, 104, pp. 765-770, (1948)) intra-carotid a 133-Xenon injection (see, for example, D. H. Ingram and G. Frazer, Distribution of cerebral activity in chronic schizophrenia, *Lancet*, 2, pp. 1984-1986, (1975)) and recently 133-Xe inhalation technique (see, for example, B. L. Mallet and W. Veall, Measurement of regional cerebral clearance rates in man using Xenon-133 inhalation and extracranial recording, *Clinical Scieces*, 29, pp. 179-197, (1965) and E. F. Duffy, J. L. Burchfiel, and C. T. Lombroso, Brain electrical activity mapping (BEAM): a method for extending the clinical utility of EEF and evoked potendial data, *Annals of Neurology*, 5, pp. 309-321, (1979)) have been applied to measure the rCBF. The 133-Xe inhalation technique provides non-invasive measurements of rCBF in both hemispheres of the brain simultaneously. The 133-Xe gas in trace amounts is inhaled by the patient, and clearance of 133-Xe from the brain is measured by conventional extracranial scintillation detectors. This technique has been applied extensively in the study of normal subjects and in clinical populations, and has several advantages, such as, (i) it is non-invasive, (ii) the 133-Xe isotope is inexpensive and commercially available, (iii) the radiation dose to the patient is relatively small, (iv) it can be used for multiple measures of rCBF on the same patient, thus allowing the study of changes during the cognitive activation process, and (v) the equipment is transportable making bedside evaluations feasible.

BRIEF SUMMARY OF THE INVENTION

One of the primary objects of the invention is to provide an improved method and apparatus for analyzing behavioral, neuropsychological and physiological functioning of a patient's brain and displaying a topographical map of the information.

A more particular object of the invention is to provide a novel method and apparatus for manipulating physiological information from a patient's brain using computer software to provide a video display of topographical maps of salient information.

A further object of the invention is to provide a novel method and apparatus for manipulating behavioral information from a patient's brain using computer software to provide a video display of topographical maps of behavioral information.

An additional object of the invention is to provide a novel method and apparatus for manipulating neuropsychological information from a patient's brain using computer software to provide a video display of topographical maps of information.

Another object of the invention is to provide a novel method and apparatus for generating a topographical map of physiological information from a patient's brain the information derived from measurement of EEG information collected during physiological testing of a patient.

An additional object of the invention is to provide an improved method for accumulating a data base of topographical maps of funcational information on the human brain by comparing physiological information and behavioral test or task results.

Another object of the invention is to provide a method of measuring EEG activity from a patient during application of neuropsychological testing of a patient and converting the EEG activity into a topographical map of behavioral type information.

In accordance with the invention an apparatus and method is provided for measuring and displaying topographical maps of brain electrical activity signals and various information processed from selected tests and tasks performed by a patient. Various computer software programs are employed to process and analyze the measured signals and information to generate interpolated topographical map outputs of the brain electrical activity signals and other processed information. These topographical maps are used for detailed diagnosis and evalution.

A user can select for display a plurality of topographical maps which illustrate various characteristics of brain electrical activity signals and other processed physiological, neuropsychological and behavioral information. For example, such physiological information as brain electrical activity and rCBF are measured by electrode sensors and scintillation detectors, respectively, and produce input activity signals. These input activity signals are interpolated to generate an expanded finer matrix of interpolated values. Interpolation is selectively performed every other pixel line in an interlace mode of constructing the topographical map. The display of data includes a color code scale and associated numerical values for determining the relative magnitudes of regions of the topographical map. In addition to the topographical maps, individual characteristics waveforms and other associated parameters can be simultaneously output to a video display or printer for comparison and association with the topographical maps.

The apparatus also operates responsive to selected software programs which are directed to the following areas: (1) accumulation of raw test results from selected tests or tasks, such as a battery of neuropsychological test or behavioral tests and calculation of an output signal weighted in terms of the expected spatial location for the information on the scalp area for a particular test, (2) during physiological and neuropsychological testing, comparison and correlation of EEG, EP and rCBF and other such measurements to test and task results in terms of topographical maps, (3) performance of montage analysis to identify by an iterative procedure features of interest in the measured EEG or EP signals, (4) performance of threshold activation analysis wherein the incoming signals are not measured and analyzed until a predetermined threshold condition has been achieved, (5) performance of a cognitive testing routine in a single testing period by applying a plurality of stimuli and sorting the associated responses with a computer, (6) performance of a Fourier transformation of EEG signals to determine frequency energy band output for the major frequency banks, and (7) performance of integration analysis of EP responses to present an averaged sum of response amplitudes to enable the user to isolate the most significant spatial and time segment contributions to the EP response and to condense the EP response spectrum to a few topographical maps. Other simple mathematical operations such as first and second order differentials and arithmetic differences of the signal also enable characterization of the patient response and allow comparison with normal population responses to isolate abnormal responses for clinical diagnostic purposes. The apparatus also can utilize external means for processing, analyzing and output of the topographical maps at a location removed from the locations at which signals are measured.

Further objects and advantages of the present invention, together with the organization and manner of operation thereof, will become apparent from the following detained description of the invention when taken in conjunction with the accompanying drawings wherein like reference numerals designate like elements throughout the several views.

BRIEF DESCRIPTION OF THE DRAWINGS

FIG. 2 shows a top view of positions of an electrode sensor arrangement with respect to a patient head outline;

FIG. 3 is an array of electrode sensors and a superimposed matrix image of a line-by-line interpolation of signals for the array;

FIG. 6 is a block diagram of a noise signal evaluation procedure;

FIG. 7 is a display output of a plurality of topographical maps of evoked potential response measurements integrated over the time intervals shown;

DESCRIPTION OF PREFERRED EMBODIMENTS

A. Brain Electrical Activity

Figure 1:
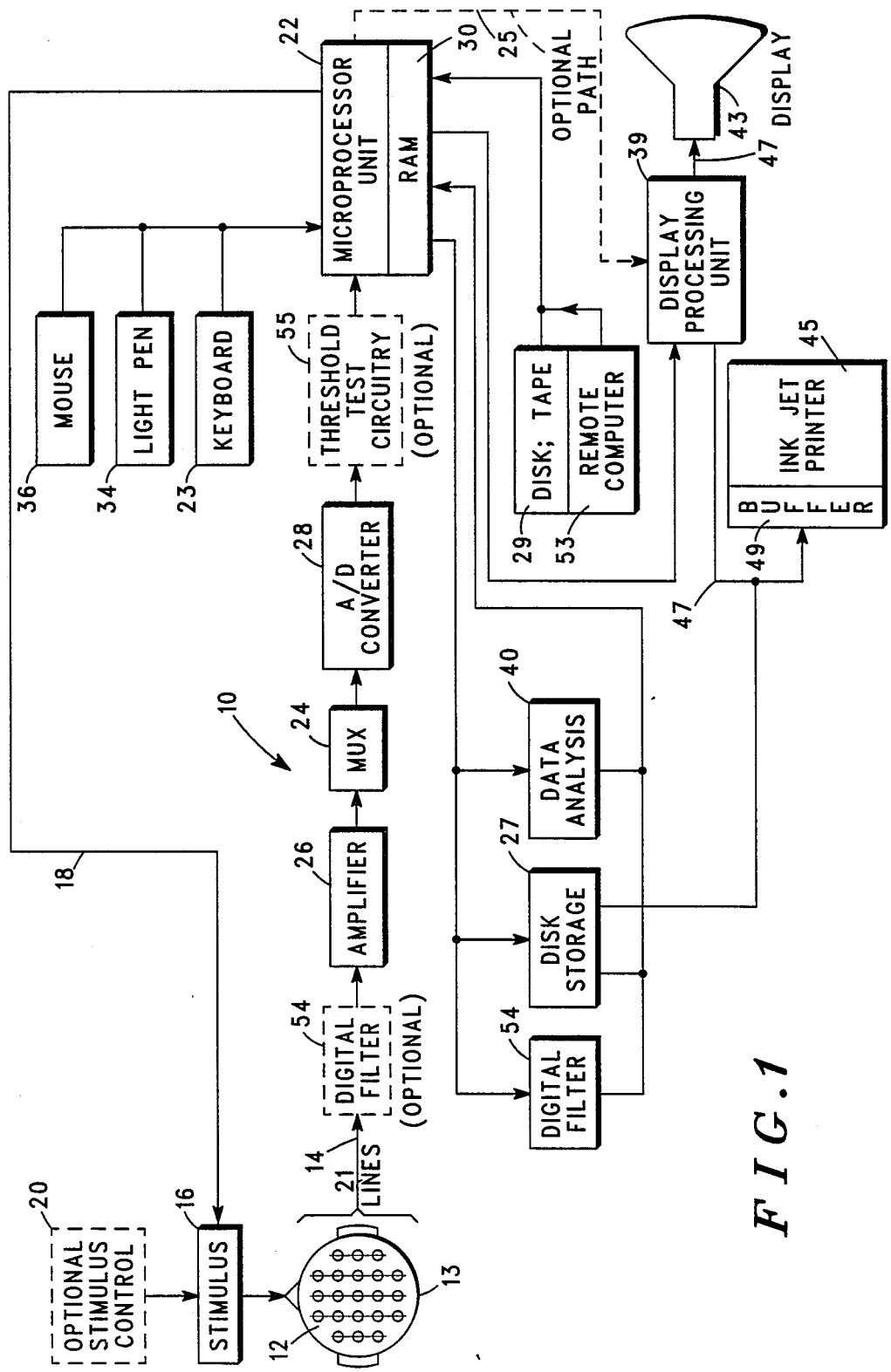
FIG. 1A is a block diagram of an apparatus for measuring brain electrical activity signals and for displaying topographic maps characteristic thereof.
FIG. 1B is a functional block diagram showing the flow path through the apparatus of measured input activity signals.

Referring now to the drawings, and in particular to FIG. 1A, a block diagram of a brain electrical activity mapping apparatus is indicated generally at 10. For purposes of measuring EEG and EP type information, the brain electrical activity mapping apparatus (hereinafter referred to as the apparatus 10) includes sensor means, such as, for example, a set of electrode sensors 12 (for example, Grass gold cup manufactured by Grass Corporation) arranged on the top of a patient's head 13. In FIG. 2 is shown an enlarged detail of an arrangement for a rectangular array or matrix of twenty-one of the electrode sensors 12 positioned on the patient's head 13. The arrangement illustrates one acceptable variety selected from various conventional international formats. In response to brain electrical activity the electrode sensors 12 generate input activity signals 14. Remote means, such as the sensors 12, can be located at remote sites as part of a distributed system for performing measurements of information on the brain, such as the signals 14. These remote measurements can be communicated through remote apparatus, such as interface devises coupled to modems, to a central location for analysis by the remainder of the apparatus 10 described hereinbelow.

In selected operating modes of the apparatus 10, such as in measurement of EP response, a stimulus 16 is also applied to the patient, and in response to the stimulus 16 the resulting brain electrical activity is sensed by the electrode sensors 12. A detailed discussion of conventional EP response measurements is set forth in Duffy et al., "Brain Electrical Activity Mapping (BEAM)" A method for Extending the Clinical Utility of EEG and Evoked Potential Data," Annals of Neurology 5, Apr., 1979, pp.209-231; which is incorporated by reference herein. The type of stimulus 16 used in EP response measurements is, for example, a strobe light, a sound (such as a click generator) or a somatosensory stimulus, such as mild electrical shock. These stimuli 16 can be periodic, aperiodic and can also be combinations of each available type of stimulus 16. In the illustrated embodiment of FIG. 1A, the stimulus 16 is controlled responsive to a control signal 18 from a main computer, such as a microcomputer unit 22. The type of stimulus 16 is selected by a user input, such as a keyboard 23. The stimulus 16 can also be provided responsive to a stimulus controller 20 which is a separate microcomputer or is a remote control source.

In other modes of operation of the apparatus 10, such as in electroencephelogram (hereinafter "EEG") measurements, the stimulus 16 is not applied to the patient. However, the measurement of brain electrical activity in the EEG mode otherwise follows substantially the same steps as for EP measurement. Therefore, in general as shown in FIG. 1A, the sensed input activity signal 14 is output from the electrode sensors 12 to processing means which includes an analog multiplexer 24, an amplifier 26 and an analog to digital converter (A/D) 28. If a Grass or Beckman polygraph is used, the electrode sensors 12, the multiplexer 24 and the amplifier 26 are included in the polygraph.

In the illustrated embodiment the amplifier 26 comprises a plurality of twenty-one amplifiers, each connected to an associated one of the electrode sensors 12. The multiplexer 24 accepts from the amplifier 26 each of the amplified input activity signals 14, and outputs each of these input activity signals 14 is serial fashion to the A/D converter 28 (for example, a Dual Systems AIM 12). The A/D converter 28 provides to the microcomputer unit 22 an amplified and digitized, or a converted, form of the input activity signal 14. In general, processing means includes those components of the apparatus 10 which operate on the signals output by the electrode sensors 12 to provide the amplified and digitized form of the input activity signals 14. The processing means can also be combined with the sensors 12 to form a remote sensor means (for example, a commercial polygraph) at a location remote from the remainder of the apparatus 10. In the manner discussed hereinbefore, the data from the polygraph is then communicated by a modem to the centrally located remainder of the apparatus 10 which analyzes the data to provide an output for display.

The microcomputer unit 22 in FIG. 1A can be any one of a plurality of commercially available computers, such as, for example, a Zenith Z-100, which uses an 8088 central processor chip (see, Intel Component Data Catalog, Jan. 1982, pp. 8-25 to 8-51, which is incorporated by reference herein). The Zenith Z-100 also includes the keyboard 23, a display processing untill (hereinafter "DPU") 39 which will be described in detail hereinafter, a disk drive (not shown) and on board random access memory (hereinafter "RAM") 30, and PROM and ROM (not shown) memories. The microcomputer unit 22 controls collection, manipulation and output of the input activity signals 14. In a preferred embodiment, the microcomputer unit 22 includes the RAM 30 which functions in part as an averaging means for storing at predetermined locations a running accumulation of the plurality of input activity signals 14. The microcomputer unit 22 adds the incoming value for the signals 14 to the previous value and stores the total in the RAM 30 at the predetermined locations. This accumulation of the amplified and converted input activity signals 14 results in statistical averaging of the input activity signals 14 which improves the signal to noise ratio. Under typical operating conditions one to ten minutes of data averaging is desirable to obtain statistically meaningful values for the input activity signals 14.

The apparatus 10 controls data gathering and analysis responsive to software programs stored on a disk or tape 29, and the program are read into the RAM 30 and executed by the microcomputer unit 22. The user interacts with the microcomputer unit 22 through input means to supply an input signal responsive to a user input. Examples of input means include the keyboard 23, a light pen 34 and a mouse 36. The user can also supply an input signal by transfer of information already stored on a disk storage unit 27 or stored in the disk or tape 29, or stored in a memory external to the apparatus 10, such as the time period of data taking, the number and type of the stimuli 16 and the desired software programs to manipulate the data for output and display for user analyzation.

Figure 1B:
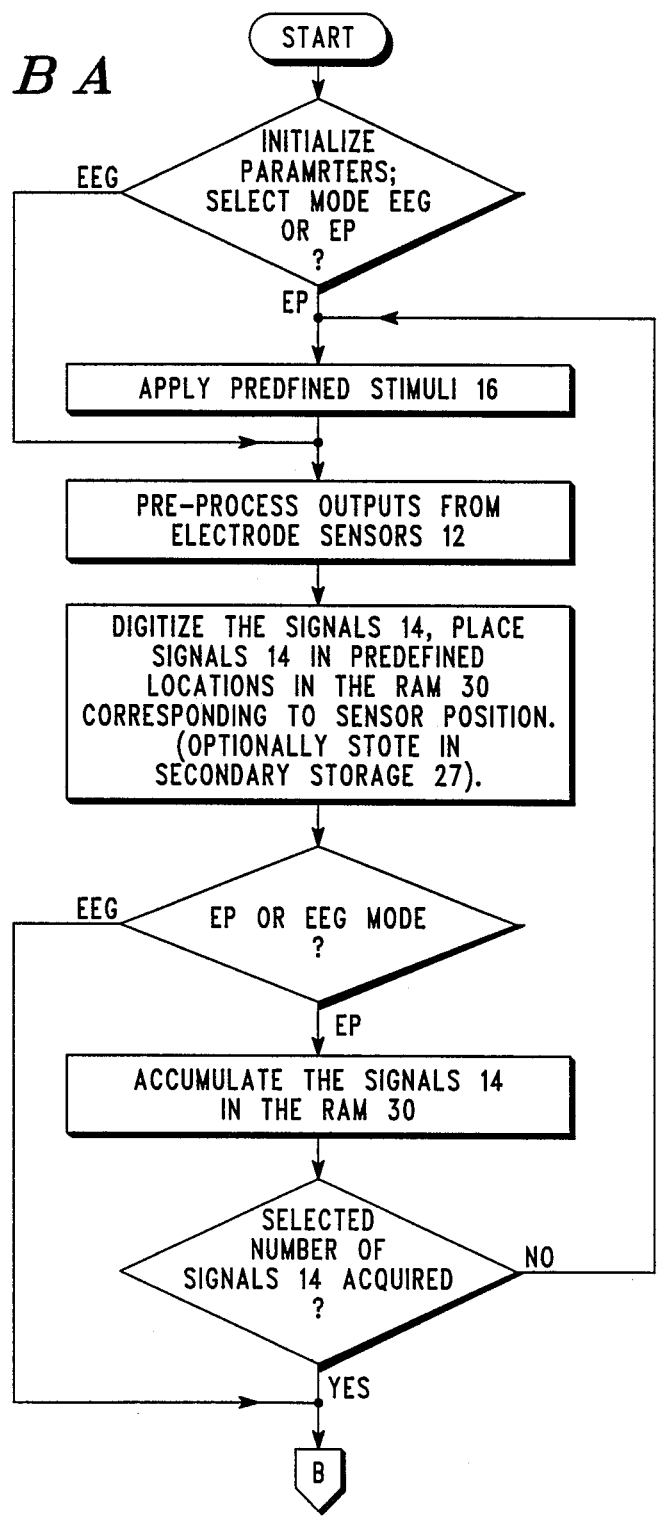
Figure 1B:
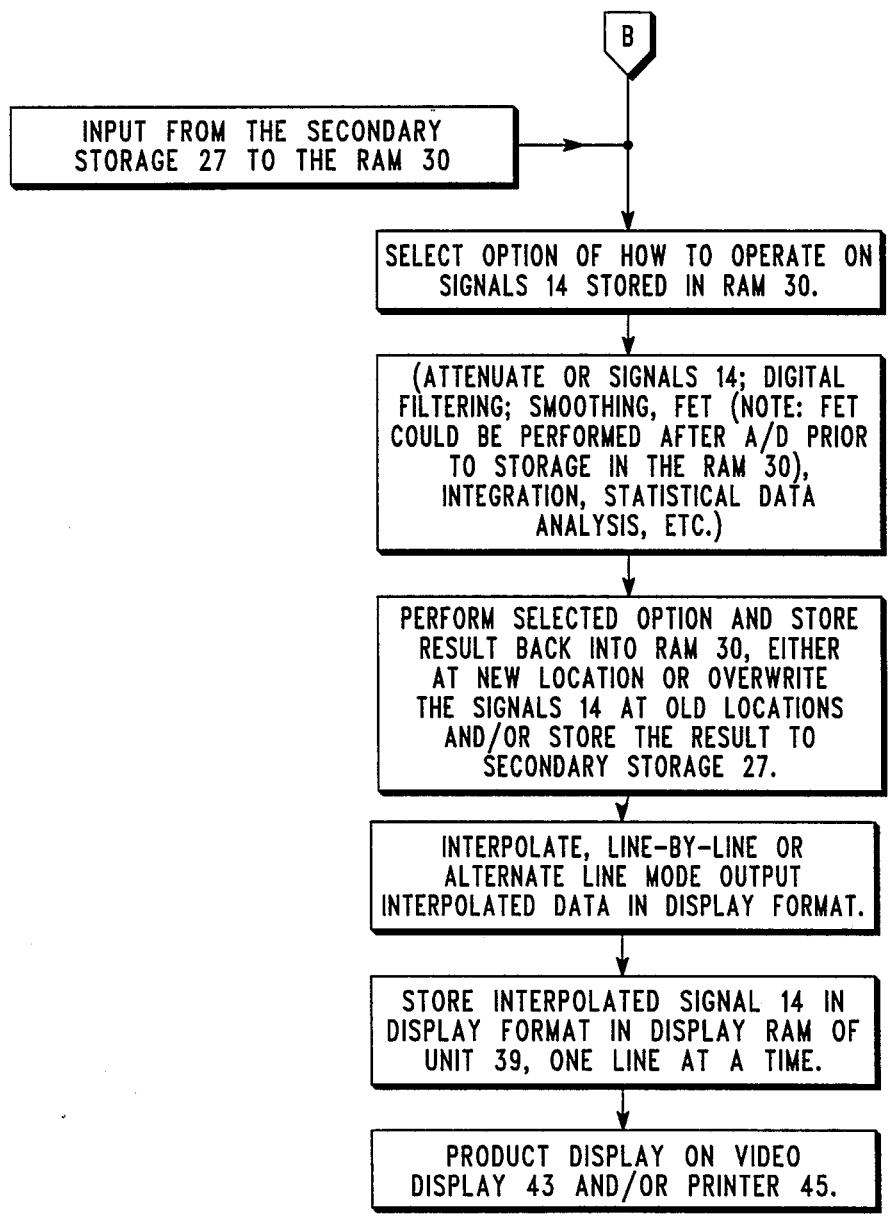

The operation of the apparatus 10 as illustrated in FIG. 1A can be better understood by reference to the procedural and signal flow diagram of FIG. 1BA and 1BB. As illustrated in FIG. 1BA, the apparatus 10 in the first decisional block has been initialized with user selected parameters or default parameters, and a mode of operation is selected. If the EP response mode is selected, then a predefined stimuli 16 is applied to the patient as a first step. However, if the EEG mode is selected, then there is no externally applied predefined stimuli 16, and the electrode sensors 12 detect EEG signals directly from the patient's head 13. In any event whether the signals originate from the patient as an EEG signal, an EP response signal or other information (such as test or task results) collected on the brain, the next step is directed to preprocessing the outputs from the electrode sensors 12. This preprocessing can include, for example, a number of steps, including amplification, hardware filtering, software filtering and fast Fourier transformation.

The preprocessed outputs from the electrode sensors 12 are then digitized, and the digitized form of the signals 14 are placed in predefined locations in the RAM 30 corresponding to predefined sensor positions. The signals 14 corresponding to particular sensor positions can alternatively or additionally be stored in secondary storage, such as the disk storage unit 27 or the tape 29.

Once the signals 14 have been digitized and stored in the RAM 30, a determination is made whether the apparatus 10 is in the EEG or the EP mode. If operating in the EEG mode the procedure skips to step B shown in FIG. 1BB. If, however, the apparatus 10 is in the EP mode, the signals 14 are accumulated in the redefined locations in the RAM 30 and/or can be stored in the disk storage unit 27 or the tape 29. Operation of the apparatus 10 then proceeds to determine whether the selected number of signals 14 have been acquired in accordance with the initial setup parameters. If the selected number of the signals 14 has been acquired in the appropriate manner, processing proceeds to step B which continues in FIG. 1BB. If, however, the selected number of the signals 14 has been not acquired, then processing resumes at the step of applying the predefined stimuli 16. This operation of the apparatus 10 in the EP mode shown in FIG. 1BA continues until the selected number of the signals 14 have been acquired.

Referring to FIG. 1BB, the operation continues at step B from FIG. 1BA. At this point the RAM 30 contains data representative of the accumulation of the digitized signals 14 at predefined locations in the RAM 30 corresponding to respective sensor positions. Alternatively, at this point, accumulated data signals can be input from a secondary storage source, such as the disk storage unit 27, to the RAM 30 to provide the initial database from which further manipulation proceeds. The next step in the operation is the selection of one of a plurality of options as to how to operate on the signals 14. Once the option is selected, the apparatus 10 proceeds to perform the appropriate operations on the signals 14 as stored and accumulated in the RAM 30. These operations on the signals 14 can include, for example, attenuation or amplification, digital filtering, smoothing, fast Fourier transformation, differentiation, integration and statistical data analysis. These operations can also be performed prior to storage in the RAM 30, such as after the A/D conversion 28 and prior to initial storage in the RAM 30.

After the selected option has been performed, the result of the operation is stored again in the RAM 30, either at new locations or at the previous locations, such as by overwriting the previous locations with the new form of the signals 14. Alternatively or additionally, the results can be stored in a secondary storage such as the disk storage unit 27. At this point, the signals 14 stored in the RAM 30 provide the basis for interpolation, either line by line or in an interlaced or alternate line mode of output, and the interpolated form of the signals 14 is output n a display format compatible with the DPU 39. The DPU 39 therefore receives and stores the interpolated form of the signals 14 in the display RAM of the DPU 39, one line at a time, as shown in the next block of FIG. 1BB. The DPU 39 generates an image on a display means, such as a video display 43 (for example, a Zenith ZVM-133), or the image is output to another form of the display means, such as an ink jet printer 45 (for example, a TRS 80 CGP220 manufactured by Tandy Corp.).

Interpolation Example

In the apparatus illustrated in FIGS. 1–7, the input activity signals 14 stored in the RAM 30 undergo an interpolation within the RAM 30 under control of the microcomputer unit 22. An expanded matrix is formed of finer resolution (for example, a forty by forty array of points in the preferred embodiment) than the arrangement of the twenty-one electrode sensors 12. The general technique of interpolation using three points to form finer resolutions frames of the input activity signals 14 is known (see, for example, Duffy et al., "Brain Electrical Activity Mapping" referred to hereinbefore). The present example of an interpolation method uses a set of two points to generate and output line-by-line of the interpolated form of the input activity signals 14.

In one preferred embodiment, a line is one line of pixels, wherein a pixel is the smallest picture element used to construct the video image. As will be described in more detail hereinafter, each pixel color is described completely by three bits of digital information stored in the RAM 30. A color mapping procedure can also be used to assign color values to the pixels. For example, each pixel can have five bits in the RAM 30 to describe one of thirty-two possible color choices which points to a color map also located in the RAM 30. The color map can have a preselected number of n bits of information which describes each of $2^2$ possible colors, and the color map digital description is output to the intensity digital to analog converter part of the DPU 39 for display of the desired pixel color.

Upon completion of the interpolation for a given line, the interpolated values can also be stored in a disk storage unit 27 for future use and analysis. A video output 37 of the interpolated input activity signals 14 is output line-by-line to the DPU 39 (preferably contained within the microcomputer unit 22 as discussed hereinbefore) in preparation for output to the video display 43. The interpolated form of the signals 14 can also be output from the RAM 30 or the DPU 39 for hard copy printout n the printer 45 or for completion of an additional data analysis 40 before being displayed. These alternative operations will be discussed in more detail hereinafter.

Figure 4A:
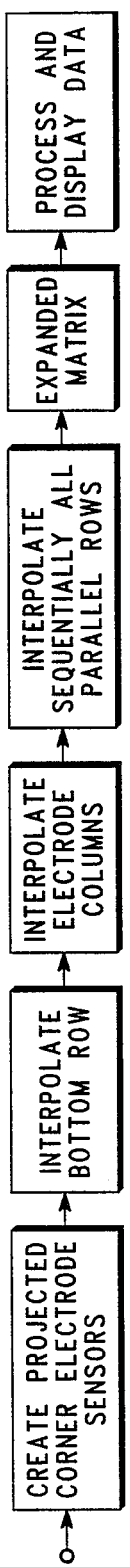
FIGS. 4A and 4B are block diagrams of two alternative methods for line-by-line interpolation and output of signals.
Figure 4B:
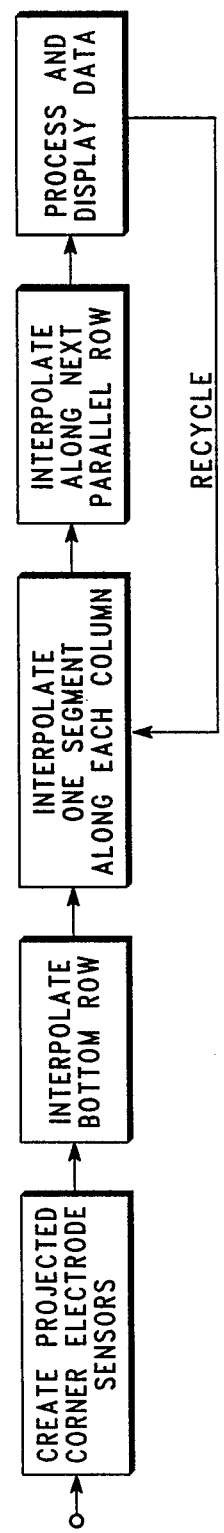

In the illustrated embodiments of FIG. 3 and FIGS. 4A and 4B, the interpolation begins by generating amplitudes at four projected electrode sensors 31 at the corners of the matrix of the electrode sensors 12 to establish a rectangularly symmetric five by five matrix of the input activity signals 14. The values for the four signals 14 at the projected electrode sensors 31 are interpolated from a linear average projection from the intersecting perpendicular lines of the electrode sensors 12 which converge n each of the projected electrode sensors 31. Once the signals 14 have been established at each of the projected electrode sensors 31, the interpolation proceeds by selecting a first line, such as a line 33 in FIG. 3 along the perimeter of the matrix of the electrode sensors 12, and starting with line 33 the line-by-line interpolation is carried out parallel to the line 33.

The use of a commercial polygraph unit with, for example, twenty-one of the electrode sensors 12, rather than twenty-five actual sensors for the five by five matrix, enables of a standard unit of substantially lower cost to the user. Further, the approximately rectangular arrangement for the twenty-one electrode sensors 12 enables the interpolation procedure to be simplified. In FIG. 4B interpolation is shown to proceed along lines which are parallel to one another and which passes through the regular array of points defined by the rectangular arrangement of the electrode sensors 12. Therefore, the interpolation takes place along one-dimensional lines which are easily defined in the rectangular arrangement, and interpolation calculations are performed more easily using only two points to generate a bracketed intermediate point. In prior conventional interpolation approaches, three points from a non-rectangular arrangement have been used and a set of coefficients precalculated for the expanded matrix of points (see, for example, U.S. Pat. No. 4,417,591, which is incorporated by reference herein).

As shown in FIG. 4A, after determination of the signals 14 at the projected electrode sensors 31, the linear interpolation is carried out for selected points a predetermined fraction of the distance between each nearest neighbor pair of the signals 14 in a column 25 of the electrode sensors 12. An interpolated value for the selected point is determined by forming a linear average of an appropriate pair of signals 14, such as the two input activity signals 14 at a pair of the electrode sensors 12. Alternatively, the pair is one of the signals 14 at one of the electrode sensors 12 and one of the projected sensors 31, which bracket the location of the selected point. For example, in the illustrated embodiment of FIG. 3 the distance between each of the electrode sensors 12 is divided into eight parts. Thus, if the selected point is one-eighth of the distance between a first one of the sensors 12 and a second one of the sensors 12, then the value for the electrical activity signal 14 at the interpolated point is seven-eighths the value of the signal 14 at the first sensor 12 plus one-eighth the value of the signal 14 at the second sensor 12. This interpolation procedure continues sequentially up each of the columns 25 of the electrode sensors 12 until the interpolation is complete for all five of the columns 25 which are perpendicular to the line 33. The interpolation is then performed for all remaining lines parallel to the line 33, proceeding incrementally from line 33 to line 35 and to the other lines until completion.

In another form of interpolation shown in FIG. 4B, after the interpolation along the line 33 has been completed, the interpolation proceeds point by point for the line 35 and for each of the subsequent lines parallel to the line 33. This procedure is accomplished by first determining the signal 14 at the selected point which is a predetermined fraction of the distance between the electrode sensor 12 contained in the line 33 and the nearest electrode sensor 12 in the same column 25. This process is completed for only a first point in each of the five columns 25 of the electrode sensors 12. The resulting five points are shown in FIG. 3 as interpolated values 38 which lie at the intersections of the columns 25 and the line 35. These values 38 are then used to complete the interpolation along the line 35 in the same manner as described above for the embodiment of FIG. 4A. Interpolated values 41 are constructed from a linear averaged combination of the appropriate pair of the interpolated values 38 which bracket each of the values 41. The line 35 is then output for presentation on the video display 43. The outputted form of the signals 14 comprising the line 35 are therefore generated in a compatible format for the conventional video display 43. Further details of operation of the video display 43 can be obtained by reference to the Zenith ZVM-133 operating manual, which is incorporated by reference herein. Alternatively, the line 35 is output for the additional data analysis 40 prior to display, depending on the user selected operational mode. Display of the complete frame of a topographical map 44 shown in FIGS. 5 and 7 continues line-by-line, incrementally completing the interpolation for each of a plurality of lines and outputting each of the lines to the video display 43.

These interpolation procedures enable the live time line-by-line processing of the input activity signals 14 for output to the video display 43. The live time output and display of the signals 14 is accomplished without having to await formation of the entire video frame and also without having to store in the RAM 30 a plurality of the lines or a complete frame of the input activity signals 14 before output to the video display 43. Prior to "live time" methods have required storage of the complete frame before the topographical map 44 could be displayed (see, for example, U.S. Pat. No. 4,417,591, which is incorporated by reference herein). Further, as mentioned hereinbefore, the line-by-line interpolation described herein requires only two end points to perform the procedure, and this greatly simplifies the calculation and storage of values in the RAM 30 and decreases the calculation and display time.

The input activity signals 14 can also undergo other operations prior to the data interpolation, such as the data analysis 40 (for example, data smoothing and a digital filtering treatment to be discussed in more detail hereinafter). Another example of the data analysis 40 is the performance of a Fourier transformation of the EEG form of the input activity signals 14 from the twenty-one electrode sensors 12. In order to avoid performing time consuming Fourier transformation for the larger number of values in the expanded frame containing the interpolated values 38 and 41, only the small numbers (twenty-one in the illustrated embodiment) of the unexpanded input activity signals 14 undergo Fourier transformation. Interpolation expansion to a finer matrix is generally done more efficiently on the data after completion of any extensive or complicated form of signal treatment, such as the Fourier transformation operation.

Video Display

In one preferred embodiment shown in FIGS. 1-7, after the interpolation and the optional data analysis 40 of the input activity signals 14, the resulting video output 37 is applied to the DPU 39 contained in the Zenith Z-100 unit. Alternatively, the raw input activity signals 14 accumulated in the RAM 30 can be output as a raw signal 25 by the microcomputer unit 22 to the DPU 39 without further processing, including interpolation. The video output 37 input to the DPU 39 is converted into an output signal 47 suitable for the video display 43 which provides the video presentation of the topographical map 44.

In the preferred embodiment there is one display rate, other than manually sequencing through the set of frames, for dynamic display of the change in EP response as a function of time elapsed after the stimulus 16 has been applied to the patient's head 13. The display rate can also be increased by generating reduced sizes of the topographical maps 44, in a manner to be described in detail hereinafter. Operation of a typical form of the DPU 39 has been discussed hereinbefore in the *Interpolation Example* section and is also explained in, "Fundamentals of Computer Graphics," J. D. Foley and A. Van Dam, Addison-Wesley Co., Reading, MA, 1982, pp. 112-136, which is incorporated by reference herein. Also, see U.S. Pat. Nos. 4,121,283, 4,139,838 and 4,213,189 which are incorporated by reference herein.

In addition to the generation of the video display 43, as mentioned hereinbefore the interpolated input activity signals 14 are selectively stored in the disk storage unit 27 or applied to the ink jet printer 45 which provides a hard copy printout of the topographical map 44.

The user selects print out of the topographical map 44 on the video display 43 by actuating transfer of the video output 47 to a page buffer 49 coupled to the ink jet printer 45. Upon filling the page buffer 49, the printer 45 outputs the hard copy printout.

Figure 5:
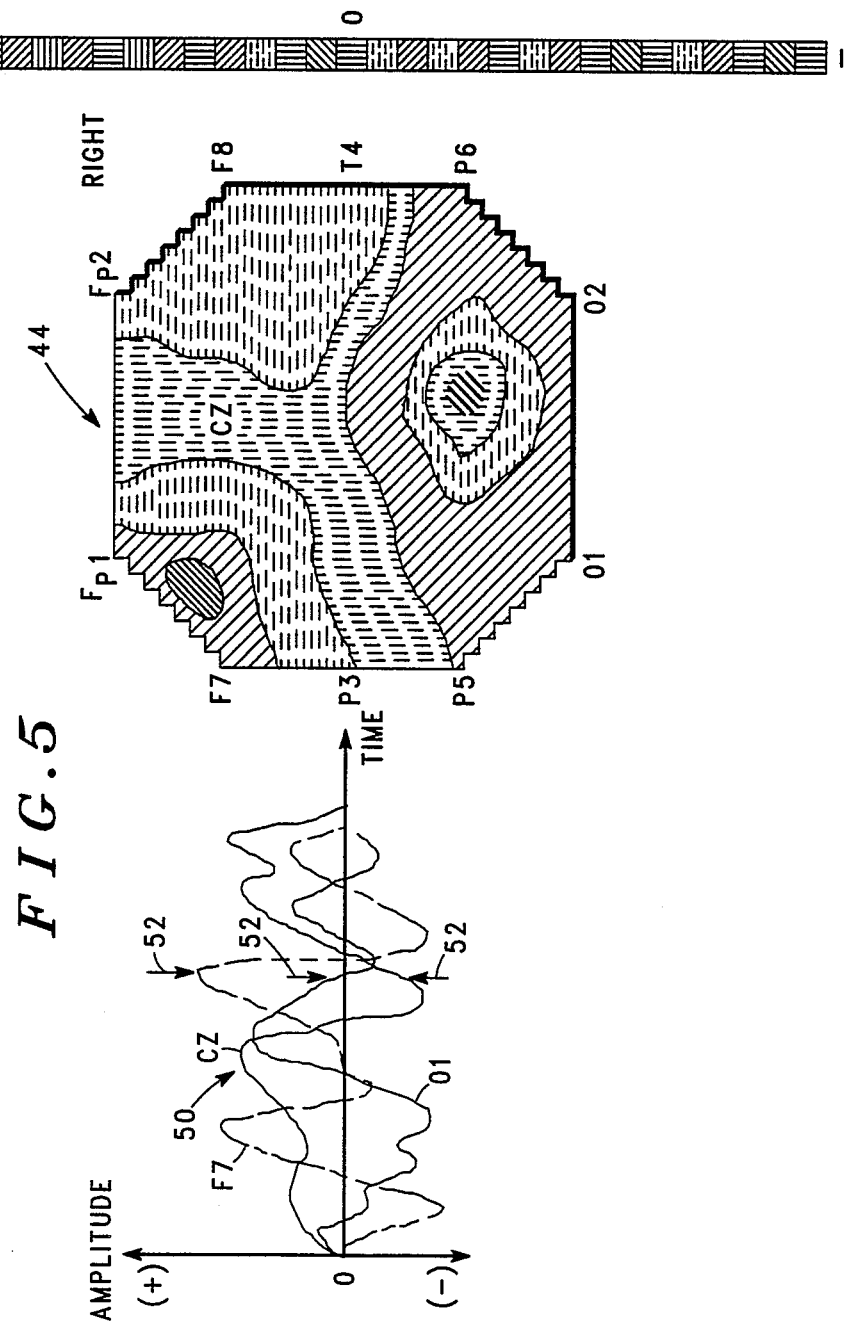
FIG. 5 is a display output of evoked potential (EP) response measurements showing a topographical map, associated waveforms for selected electrode sensor locations and a vertically positioned color code scale.

In the illustrated embodiment of FIG. 5, the topographical map 44 is color coded, and thirty-two different color choices can be used to encode the relative magnitude of the brain electrical activity for the input activity signals 14 displayed on the topographical map 44. In the illustrated embodiment of FIGS. 1 and 5, color code means for encoding the colors on the topographical map 44 is accomplished in conjunction with a software program which is read into the RAM 30 from the disk 29. The topographical map 44 is constructed of blocks of two by four, or eight, pixels; and as mentioned hereinbefore each of the pixels in the block are described by three separate storage bits, one for each of the memory locations in the RAM 30 associated with the red, green and blue colors which are used to construct all the colors. With three storage bits per pixel a total of two cubed, or eight, unique colors can be constructed. These eight colors, along with white, are assigned to individual pixels in the block and are mixed to generate twenty-four more colors. For example, the block of two by four pixels can be constructed in a predetermined manner using the unique colors to arrange the colors of near neighbor pixels around a selected given pixel to form a block having a light yellow appearance. This is accomplished by having every next nearest neighbor pixel of selected given pixel as a yellow pixel, which is described by the green storage bit as "1", and a red bit as "0" and the blue bit as "1". The remaining nearest neighbor pixels around the given pixel are white with the red, green and blue storage bits all "1". Colors for the pixel blocks other than the unique colors are constructed in a similar fashion by mixing two preselected colors in the pixel blocks in the above described manner. This method of color construction further helps to reduce the cost of the apparatus 10 which substantially enhances the commercial significance and usefulness of the apparatus 10.

In the illustrated embodiments the color coding of the topographical map 44 is graphically explained to the user by generating alongside the map 44 a vertically positioned, color column or scale 46 having different color segments 48. The thirty-two colors in the illustrated embodiment are depicted by various cross hatching and line patterns. Each of the color segments 48 represents a fixed relative magnitude within a selected closed data set of the interpolated values 38 and 41 for the input activity signals 14. A closed data set is meant to include those input activity signals 14 measured on the patient's head 13 for a fixed set of measurement variables, such as, amplifier gain and the nature of the stimulus 16.

The color scale 46 can also be positioned horizontally or is arranged alongside selected portions of any number of sides (for example, four if rectangular) of the topographical map 44. The user can also select the display of only the color segments 48 which are being used for the associated topographical map 44. This enables removal of unused colors to simplify association of colors with an amplitude at a selected location on the topographical maps 44.

In the illustrated embodiment of FIG. 5 in addition to the topographical map 44 and the color scale 46, the video display 43 also includes waveforms 50 which are characteristics of the EP response input activity signal 14 at the use selected electorde sensors 12. The user also can display the waveforms 50 associated with the interpolated values 38 and 41. Each of the waveforms 50 is output and displayed as a color coded line and also is identified using a conventional international format format with an appropriate letter and number (for example, CZ, 01 and F7 in FIG. 5). The letter and number are indicative of the selected electrode sensor 12 or other interpolated point, such as one of the interpolated values 38 or 41.

In FIG. 5 are shown examples of the waveform 50 for EP response amplitudes which vary as a function of time above and below a centered zero base line. Typically, the EP response is measured over time periods of 256, 512, 1024 or 2048 milliseconds. The topographical maps 44 appear to the viewer as a series of frames showing the outline of the patient's head 13. Each of the frames is characteristic of the EP response amplitudes at a particular time after applying the stimulus 16 to the patient. For example, each frame can represent one particular four millisecond time segment of the total set of the frames which covers the time period from zero to 512 milliseconds in four millisecond increments. Therefore, for each of the user selected locations on the patient's head 13 for one of the frames, there is displayed the associated waveform 50. A particular point on the waveform 50 describes the amplitude for a particular time segment after the stimulus 16 has applied to the patient. In order to pinpoint the time segment on the waveform 50, an indicator or a cursor 52 is displayed in FIG. 5 which points toward the segment and to the amplitude on the waveform 50.

In the display of the topographical maps 44 of the EEG input activity signals 14 the user is able to select one of the locations (such as, at one of the sensors 12 or the interpolated values 38 or 41) on the patient's head 13 and generate adjacent the EEG topographical maps 44 an EEG curve of the contribution from the various frequency bands (i.e., $\alpha$, $\beta$, $\delta$ and $\theta$). The curve amplitude is correlated to an associated one of the frequency bands by using color coded segments positioned along the abscissa, or frequency, axis of the EEG curve. The color coded segment is indicative of preselected ones of the frequency bands as the $\alpha$, $\beta$, $\delta$ and $\theta$ bands.

The user of the apparatus shown in FIG. 1 also has the ability to select the display of a plurality of reduced sizes of the topographical maps 44. This feature enables the user to display a number of the topographical maps 44 on a single screen of the video display 43 of a single page of a printed output. For example, in FIG. 7 is illustrated the display of a plurality of the topographical maps 44, along with the color scale 46. The user can also display the waveforms 50 for the same or for different locations in each of the plurality of the topographical maps 44. The user can select to display different brain electrical activity states or different types of measurements for the reduced size topographical maps 44. For example, the user can select the display of EP responses and EEG information, or EP responses characteristic of a plurality of different ones of the stimuli 16.

B. Neuropsychological Evaluation

Evaluation of the human brain in one form of the instant invention is provided by a battery of the neuropsychological tests administered to the patient in a totally non-invasive evaluation of behavioral information and performance. Since the behavioral information is related to the physiological functioning of the brain, these tests can provide significant information about functional abnormalities of the brain. Physiological functions presumably derive from structures in the brain and hence a functional abnormality very often is a manifestation on an underlying structural abnormality. These functional and structural abnormalities are typically detected using the previously mentioned neuro-imaging methods, such as XCT and PET. The development of neuro-imaging techniques for in-vivo studies of brain anatomy and physiology has created an opportunity for behavioral neuroscience to examine the brain behavior relationship by integrating the behavioral data with the anatomical and physiological data. An obstacle to this end is the lack of methods for comparative analysis as the nature of the various data sets is entirely different. A standard neuropsychological test battery typically includes measures of intellectual functions (for example, verbal, spatial and abstract reasoning), memory (semantic and figural), learning, language (expressive and receptive), perception (auditory, visual, and tactile) motor skills, attention and concentration. The performance of subjects in each of these tests is a number in the range of −a, to +a, where a is some constant and a score of zero indicates normal performance. Parameters such as age, sex, and handedness are also taken into account and negative and positive numbers indicate poorer or better than normal performance, respectively. Note that such batteries of neuropsychological tests can be interpreted by the functions which are impaired and also by the brain regions implicated in the pattern of deficits. Thus, such information does lend itself to topographical mapping.

Figure 8:
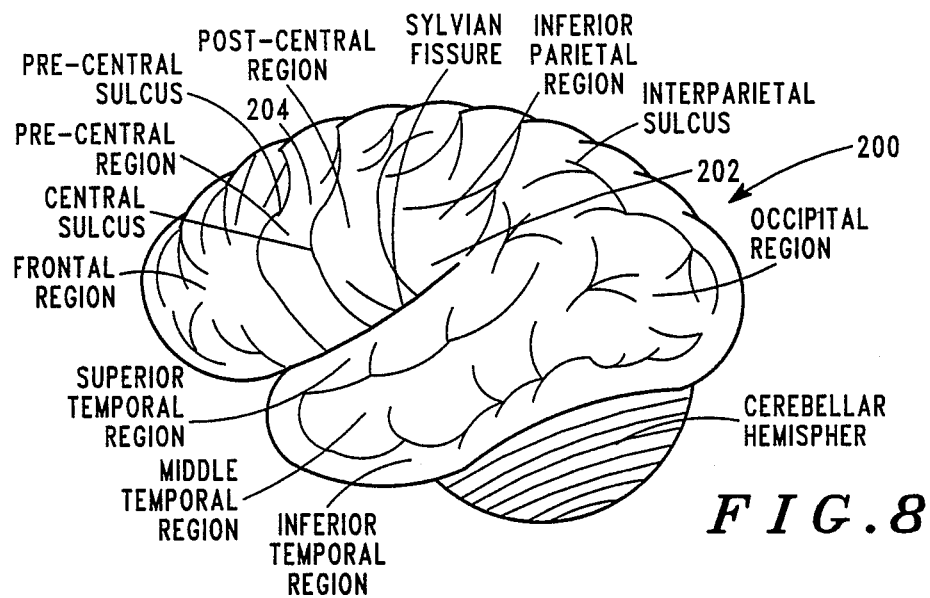
FIG. 8 is a lateral view of the human brain.
Figure 9A:
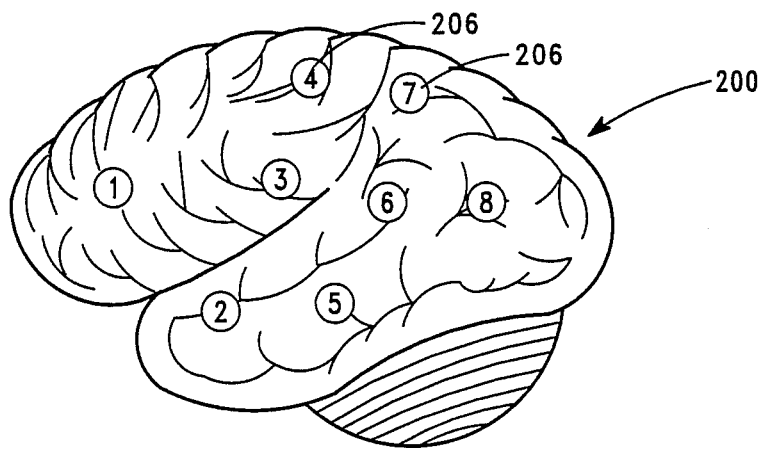
FIG. 9A shows a sixteen detector arrangement and FIG. 9B shows a thirty-two detector arrangement for measuring the rCBF.
Figure 9B:
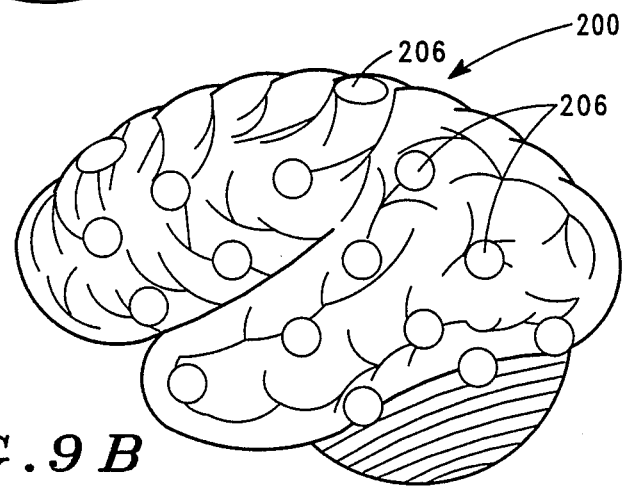

The brain can roughly be divided into certain broad areas believed to be implicated in various tasks. For example, temporal regions are generally assumed to subserve language processing whereas the occipital regions are involved in visual information processing. A lateral view of a human brain 200 is shown in FIG. 8, with most relevant areas indicated. Some of the earliest experiments for measuring the rCBF using the 133-Xe inhalation technique were conducted with only four detectors of the 133-Xe, with two associated with each hemisphere of the brain 200 measuring the blood flow in the parietal region 202 and precentral regions 204 of the brain 200. Helmets (not shown) having sixteen and thirty two detectors 206 are now commercially available, and exemplary arrangements of the detectors 206 are shown in FIGS. 9A and B. The detectors 206 have a diameter of nearly 2 cm for acceptable signal to noise ratios, and an attempt is made to orient them perpendicular to the surface of the scalp. These size requirements place a limitation on the number of the detectors 206 that can be used. Currently thirty two of the detectors 206 is the maximum number used in a study. Since the rCBF measurements are highly reproducible and since the radiation dose involved in these studies is quite small (less than 0.5 rads per study), it is possible by suitable design of the helmet to fill in the data at intermediate positions by taking two measurement sets and moving the detectors 206 by a certain amount in between measurement sets.

Once placement of the detectors 206 has been decided, one must consider the following three issues in order to generate the desired topographical maps:
  (i) determine the appropriate viewing direction;
  (ii) construct a meaningful geometrical model of the head; and
  (iii) apply suitable interpolation procedures for creating the topographical maps.

The viewing direction and the geometrical model of the head are important from the viewpoint of the analysis and interpretation of the topographical maps.

Figure 10:
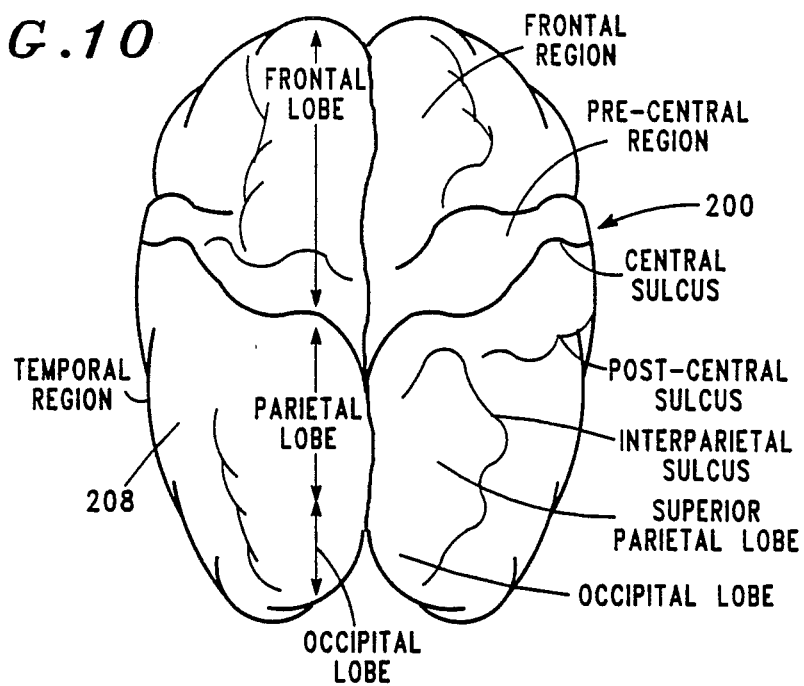
FIG. 10 is a top view projection of the human brain.

In FIGS. 9A and B we show the placement of various numbered detectors 206 in a lateral (or side view) projection of the brain 200. In FIG. 10 we show the top view of the brain 200 (of which FIG. 8 is the side view). Note that the orthographic top view projection will compress many of the areas of interest seen as separated in the side view. Similarly, the side view causes compression of the areas on the top region of the brain 200. The main purpose of using topographical mapping is to be able to comprehend and evaluate the patterns of activity and functionality associated with the normal and disease states better than is possible with presentation of numbers and graphs. To this end it is desirable to be able to view simultaneously the activity on both hemispheres of the brain 200, and the top view is a better choice. However, some corrective measures can be taken in order to accommodate the compression of selected brain areas, such as temporal region 208 in FIG. 10.

Most of the techniques for presenting the topographical maps of the EEG data use a spherical mode of the brain 200 for dipole localization (see, for example, U.S. Pat. Nos. 4,408,616 and 4,421,122 which are incorporated by reference herein). These patents utilize top down views drawn as idealized ellipses with a ten/twenty system of electrode positions for EEG mapping. A projection geometry is used in some cases, (see for example, R. Coppola et al. "Computer Generation of Surface Distribution Maps of Measures of Brain Activity," Computer in Bio Med. 12,191 (1982)) and is an equal projection scheme in which an area on the three dimensional surface is projected an equal area on the three dimensional projection. This scheme is better than earlier ones since it is easier to locate pattern features.

Figure 11A:
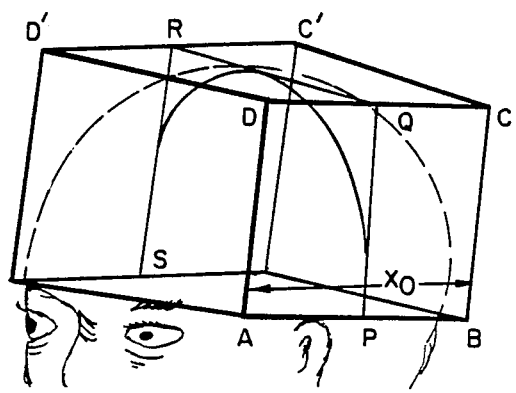
FIG. 11A shows the projection geometry used for image generation. ADCB represents the plane containing the left side view projection and CDD'C' is the top view projection plane in FIG. 11B which shows a triangular approximation to reduce the compression of the regions in the temporal lobe in the top view.
Figure 11B:
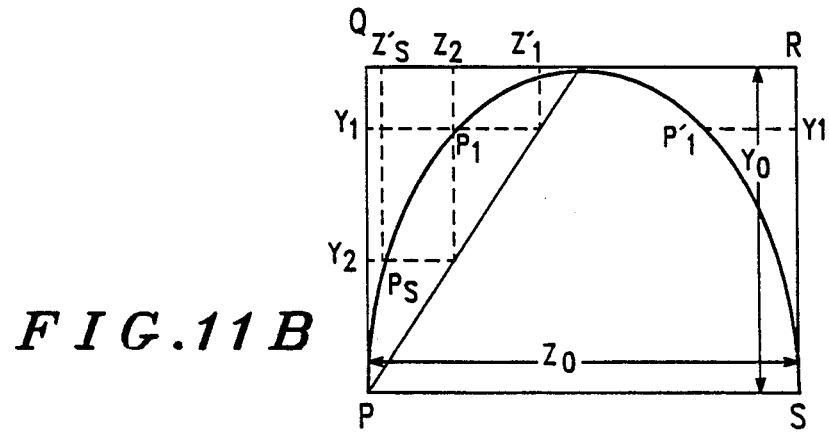

We have taken another approach to the topographical mapping of the top view of the human brain that shows two suitably mapped lateral views side-by-side. A point (x,y) in the side view is mapped into the top view using a triangular approximation as shown in FIG. 11. The origin is at D, and thus the top view projection of a point (x, y) in the side view will be (z, x), where z is given by the expression $$z = .5\left(z_0 - \frac{z_0}{y_0} y\right)$$

A point in a homotopic region on the other hemisphere will project onto (z,x) with z expressed as:

$$z = .5\left(z_0 + \frac{z_0}{y_0} y\right)$$

Here, $(x_0, y_0)$ and $(z_0, x_0)$ are the sizes of the side view and top view projections respectively. Note that $(x_0, 2y_0, z_0)$ are also the diagonals of the ellipsoid that approximates the dimensions of a patient's skull 209. The triangular approximation is chosen because it preserves the dimensions of the projected image and it produces comparatively less distortion in the top view projections, especially in the temporal regions 208, and hence makes it easier to locate important pattern features. In our preliminary studies we have found topographical mapping based on the triangular approximation to be highly satisfactory for visual inspection and evaluation of information.

Figure 12A:
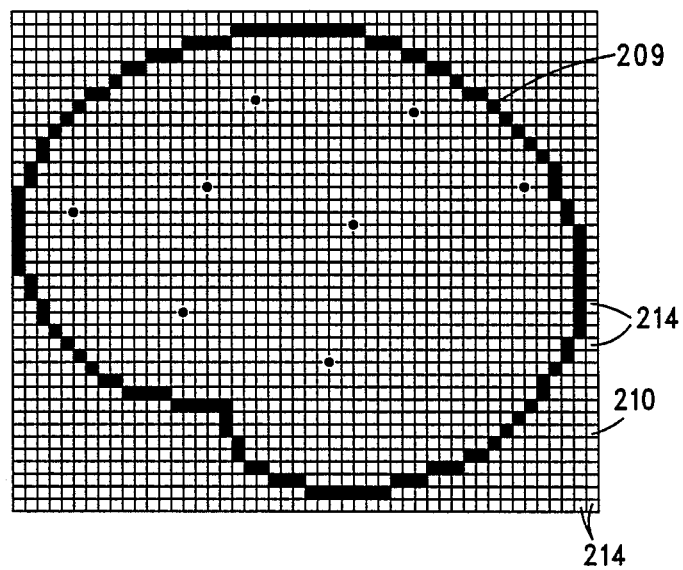
FIG. 12A is an outline of the skull projections with the superimposed grid pattern and detector arrangement on the left side view and FIG. 12B shows the top view; and, FIG. 13 shows regional weights assigned to the block design subtest of the WAIS-R (1=minimum; 10=maximum).
Figure 12B:
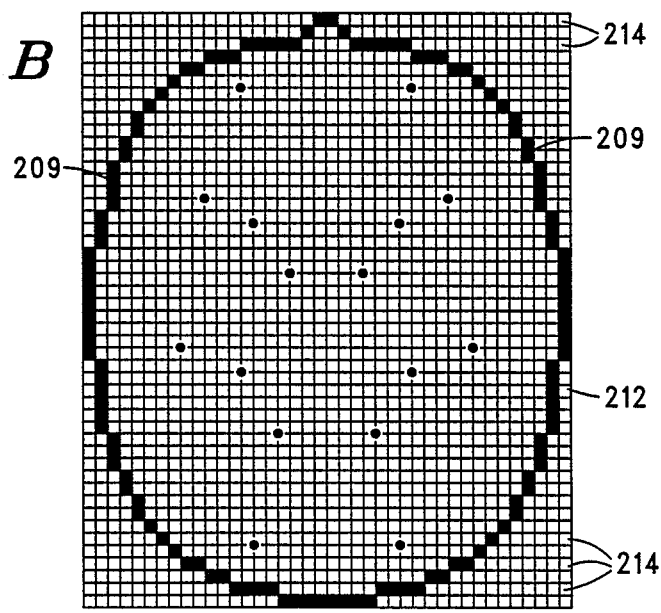

The top view projection geometry previously described enables association of every point on the surface of the patient's skull 209 to a point in the two dimensional projection of the side or the top view. Hereinafter we shall refer to the image plane as (x, y). The image generation now consists of: (i) defining the region of interest in the projection plane corresponding to the outline of the skull 209 and (ii) estimating the value of the measured parameter at a point (x,y), given the measured value of the same parameter at points $(x_i, y_i)$, i = 1, ..., N, where N is the number of the detectors 206 and $(x_i, y_i)$ is the projection of the i-th detector location in the image plane according to the triangular projection scheme. A 48×40 grid 210 is superimposed for the side view and a 40×48 grid 214 for the top view on the projection image (see FIG. 12). Each grid element 214 corresponds to a pixel in the topographical map, and the map intensity at that pixel is the estimated value of the parameter at the center of the pixel. The outline of the projection of the skull 209 was drawn on these grids 210 and 212. In one form of the invention, regions of interest can be defined in the computer software programs as a sequence of row segments, each segment represented by three numbers, namely, a row index, and the left and right end points of the region segment in the associated row. Thus, the region of interest in FIG. 12A is a sequence of numbers such as 2, 19, 29, 3, 15, 32, ..., 18, 1, 47, ..., 39, 25, and 31.

The image intensities for all the grid elements 214 (and each associated pixel in the map) in the regions of interest can now be obtained using various interpolation and extrapolation procedures (see for example, Ser. No. 646,614 which is incorporated by reference). This interpolation procedure can be accomplished by using linear averaging of the two nearest data points or bilinear interpolation which takes into account measurements at four closest detector locations. In the following example of interpolation, the three detectors closest to the grid element 214 under consideration are determined. Next, one determines whether the detectors 206 are collinear or if the grid element 214 lies outside the triangle with vertices at the closest location. If the center of the selected grid element 214 is within the triangle, then the intensity $I_{jk}$ assigned to the (j, k)th grid element 214, is the third coordinate of the point ((j−0.5)a, (k−0.5)a, $I_{jk}$) lying on the plane passing through the three points $(X_iY_i, P_i)$, where i extends over three closest detector indices. If the point ((j−0.5)a, (k−0.5)a) lies outside the triangles, or if the three locations in the projection are collinear, then the intensity assigned to the grid element 214 is the following:

$$I_{jk} = \sum_i \frac{(DSUM - D_{jki})}{DSUM} P_i$$

We have assumed the origin to be at the upper left corner of the image $D_{jki}$ is distance of the (j,k)th grid element 214 from the i-th detector located at $(x_i, y_i)$ in the projection image. $P_i$ is the measured parameter at the detector location and "a" is the size of the associated pixel. The indice i extends over the two closest detectors 206 and $DSUM = D_{jk1} + D_{jk2}$. A smoothing procedure can be incorporated by averaging the pixel intensities in a (3×3) neighborhood. The methods discussed for image generation can be used for generating both the side and the top view of the parameter under study.

Imaging rCBF

As mentioned before a number of techniques used for measuring brain activity make use of extracranial forms of the detectors 206. Data generated by such measurements for resting baseline and cognitive activity can be used to evaluate the regional patterns of abnormality associated with brain pathology. However, the ability to do so is limited by the lack of imaging. To study the effects of major factors such as age, sex, or handedness on rCBF, during, for example, rest and two cognitive tasks would require assimilation of a prohibitively large amount of data using the system having sixteen and thirty of the detectors 206. Statistical analysis of group data is essential for evaluating specific hypotheses and for examining major gradients in the brain 200, such as laterality and anterior-posterior, but such analysis may miss smoother gradients or regionally circumscribed effects. Topographical maps of extracranial measurement are likely to assist in the analysis of such details.

Measurement of the rCBF using the 133-Xe inhalation technique provides a number of reproducible quantitative indices, such as: (1) f-l, the flow of the fast clearing compartment which presumably reflects the gray matter flow, (2) Is the initial slope of the clearance curve, and (3) CBF-15—average flow in the gray and white matter. The technique has been found to be sensitive to changes in the rCBF during engagement in cognitive tasks. The parameter being displayed as a topographical map can be any relevant index of the blood flow, such as, region to whole brain ratios, laterality indices or deviation from the baseline measurement. In our implementation of the imaging method, we first create an input data file that has information about the number of the detectors 206, detector positions in the side view projections (the top view can be generated from the same input file), and the values of the indices for each of the detectors 206 corresponding to the resting baseline, verbal and spatial task. The format of the input file requires that the detectors 206 be placed in the homotopic regions of the two hemispheres of the brain 200. Thus for the sixteen detector system and three measurements (resting, verbal, and spatial) the user needs to input sixty-four numbers in all. Once the input file has been created, the process of generating the side and the top views takes only seconds. The methods have been implemented on a mini-computer, such as, for example, a Data General Eclipse S/200 had using a COMTAL raster scan display unit. The images are saved for display and recording at a later time, if necessary. The method allows window setting of gray levels for contract enhancement. Topographic maps of normal and abnormal patients can be compared and significant differences can be discerned.

Imaging of Neuropsychological Test Scores

Figure 13:
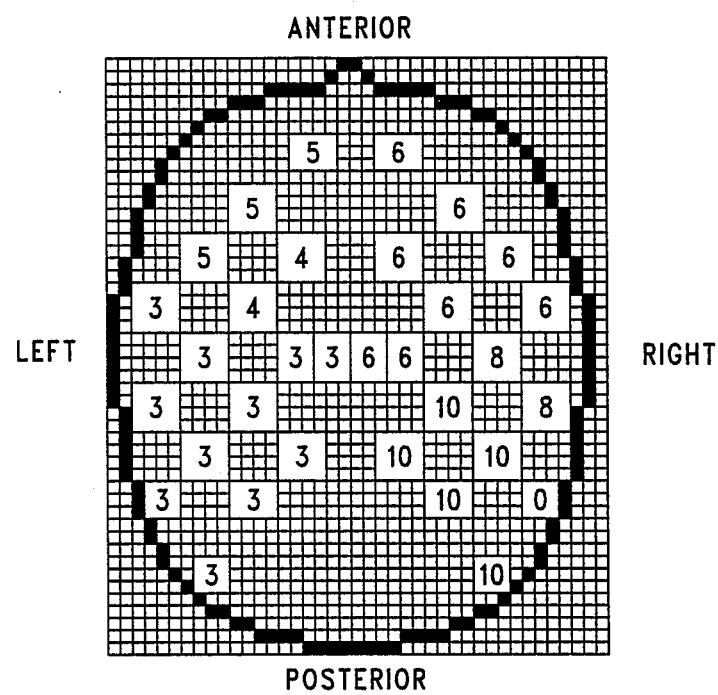

Our framework for imaging the performance of a patient in neuropsychological tests is influenced by the method for imaging the rCBF as described hereinbefore. We first divide the brain 200 into regions of interest (hereinafter, ROI) and identify each ROI by a point in the side view projection. Note that this is identical to detector placement using probability weightings of the likelihood of damage in a given ROI causing deficits on specific neuropsychological tests. The weightings are on a ten point scale which is based on current research and clinical evidence. FIG. 13 shows an example of the weights assigned to the Block Design subtest of the WAIS-R. The weights are entered in a weight table $W(i, j)$, $i=1, \ldots, N$, $j=1, \ldots, M$, where $W(i, j)$ is the weight assigned to the j-th brain region for the i-th behavioral test. There is a total of N tests and M regions of interest. The tests given to the patient must have the corresponding weights listed in the weight table, although not all the test listed in the weight table have to be given to the patient. In order to build the behavioral topographic map, we used an index Pj defined as a function of the test scores $S_i$ and the weights according to the following:

$$Pj = \frac{\sum_i W(i,j) S_i}{Norm(j)}$$

Where the summation extends over the subset of the tests given to the patient. Note that Pj can now be treated in a manner identical to the parameter of the blood flow measured by the j-th detectors 206 for the imaging purposes.

The normalizing function NORM(j) can be, for example, the number of the tests used in the calculation of Pj. However, depending on the choice of tests and particular subject prognosis, this choice may not be adequate. For example, if a patient has a lesion in the left hemisphere and is given more tests which are most relevant for detecting a lesion in the right hemisphere than in the left hemisphere, then the topographic map will not be indicative of the lesion. Such a situation can be handled by having NORM(j)=the sum of W(i, j), summed over the tests given. Note that this method will not show any variation in intensity across the image if only one test was given.

Another example normalizing function that can be utilized is based on the rationale that the tests administered to the patients are the ones relevant from the viewpoint of the regions implicated in a pattern of deficits. The tests are then weighted according to their relevance to the disorder, and the normalization is accomplished by assigning to each test score an additional weight as follows:

$$Pj = W(i, j) A(i, j) S_i, \text{ and}$$

Let $$A'(i, j) = \frac{Dj}{|W(i,j) - Wj|},$$

with $$Wj = \frac{1}{N} \sum_i W(i, j),$$

and $$Dj = \frac{1}{N} \sum_i |W(i, j) - Wj|$$

A(i, j) used in the previous equation is not defined as:

$$A(i, j) = A'(i, j) \text{ if } A'(i, j) \leq 1 \text{ and } Dj \neq 0.$$
$$= 1 \text{ otherwise or if } Dj = 0.$$

= 1 otherwise or if Dj=0.

Appropriateness of a particular normalization function depends on the rationale underlying the choice of the subset of tests administered to the patient. In the embodiment discussed in the specification the topographic maps can created using the function, $$NORM(j) = \sum_j W(i,j).$$

The use of topographic mapping techniques permits the simultaneous and instaneous evaluation of large arrays of data, and allows the identification of patterns of iso-density contours associated with various disease states.

These topographic mapping methods are also an initial step towards a systematic study of the correlations among human behavior, physiological information and anatomical data. Since the rCBF and behavioral maps are generated from a common frame of reference, they permit comparative study and the integration of two totally independent methodologies for studying brain functions, such as blood flow and behavior. The topographic maps can also be used to integrate by comparison and contrast the maps thus obtained with the data sets generated by other imaging methods, such as XCT and PET, or other measurements, such as EEG and EP brain electrical activity.

This approach can allow evaluation of physiological functioning of the brain of a patient by providing topographical maps characteristics of an abnormality. The method comprises applying a selected neuropsychological test battery to the patient, measuring the brain electrical activity associated with the patient responding to the selected neuropsychological test, operating on the measured brain electrical activity and providing weighted output signals characteristic of the physiological functioning of the patient's brain responsive to the selected neuropsychological test battery and generating the topographical map responsive to the weighted output signal. In a similar manner, the physiological functioning can be directly determined by displaying the weighted output signal calculated from the neuropsychological test results, or from a general task being done and generating information on the patient's brain.

Additional useful brain functionality information can be accumulated into a data base by carrying out a method correlating neuropsychological, behavioral or other task based test information to measured brain electrical activity. Subjects having normal and abnormal brain physiology undergo testing to generate the data base by arranging a plurality of various types of the detectors 206 on the scalp of each of the subjects. The detectors 206 can, for example, be 133-Xe sensors for rCBF measurements and conventional transducers described hereinbefore for measuring EEG or EP signals. A selected neuropsychological test battery (or other test or task) is applied to each of the subjects, and EEG activity is measured, and substantially simultaneously, various predetermined physical parameters, such as rCBF, are measured. The information is compared and a conversion matrix is generated for transforming between the measured brain electrical activity and the information, such as, behavioral neuropsychological. Finally, the conversion matrix is then performed for a sufficient number of subjects to generate a useful data base.

The data base described above can be used for analyzing the physiology of a selected patient using data bases of normal and abnormal brain physiology in the form of topographical maps. One can selectively measure and generate topographical maps and associated data from brain electrical activity measurement or predetermined tests or tasks. One can run a computer comparison of the measured response from the selected patient and compare topographical maps to determine whether any abnormalities can be determined.

Such techniques can improve the sensitivity of psychometric evaluations of patterns of regional brain dysfunction, since they are objective and not constrained by the capacity of humans to consider and evaluate large sets of numbers representing the test scores and the regional weights assigned to particular tests. These topographical maps may thus facilitate conceptualization in terms of functional systems that encompass anatomy, physiology and behavior.

COMPUTER SOFTWARE

The apparatus 10 performs an analysis of information, such as, input activity signals 14, to provide the video output 37 responsive to various means, such as for example, computer means comprises a computer software program selected by the user and the microcomputer unit 22 which executes the software program. As illustrated in FIG. 1, the computer programs stored on the disk or tape 29 and the loaded into the RAM 30 in preparation for execution by the microcomputer unit 22. The computer programs of the computer means can also be input from a remote external source, such as a remote storage device (not shown) or a remote computer 53, into the RAM 30. Alternatively the computer programs are input directly into the microcomputer unit 22 for execution therein. The ability to use the remote source for the computer programs enables the user to draw on an extensive collection of software at a central location and helps reduce capital costs for the small clinic or small group of practitioners. The means for providing the video output 37 also can generally include any form of logic means, hardware and software, which programs to analyze the amplified and digitized input activity signals 14 to generate the video output 37.

When the apparatus 10 processes the data from a remote means, such as a remotely located polygraph or an electrode sensor 12 for sensing the signals 14, the signals 14 are input to an interface means (not shown). This interface means translates the signals 14 to enable communication by a modem over a telephone line or other suitable telecommunications equipment to the processing means and to logic or computer means for analysis to generate the video output 37. Such a form of the apparatus 10 avoids the need to have a dedicated system and makes feasible the measurement of the signals 14 at remote locations and enables the use of the apparatus 10 by smaller clinics and individual practitioners who would otherwise be unable to support a dedicated system.

In the preferred embodiment, a master control program is provided as an executive which guides the user through the necessary steps for initial calibration of the apparatus 10, setting of apparatus parameters, including type of functions desired, topographical and Fourier transform data, filter characteristics, number of samples per second, display update frequency and so forth. The user calls up the executive programs which then sequences the user through the appropriate command requests to provide for various functionality as described throughout this specification. The executive can be written in any plurality of languages, including assembly language, BASIC, FORTRAN, etc. and can operate under a plurality of commercially available operating systems, such as CP/M-86, MS-DOS or UNIX, on any of the plurality of commercial systems, such as the Zenith Z-100 system given as an example hereinbefore.

Once the apparatus 10 is calibrated and necessary set-up data is provided, the apparatus 10 can provide the topographical map 44 of the brain electrical activity in either live time, as sampled data is being acquired and stored, or mapping and display of the brain electrical activity, or other such data, can be performed and stored on transferred data files not actually gathered in live time and can even be performed at an external, remote location relative to the apparatus 10. The mapping and display operation can be performed by the apparatus 10 and/or electronic hardware processing of the input activity signals 14. Hard copy printout on the printer 45 and/or output to the video display 43 can be provided at the user's selection.

In another arrangement instead of the master control program, the apparatus 10 can provide all necessary functions by providing a plurality of separate callable software routines for the user to call up at his option. In this case, no central executive program would be required.

Some of the software programs are utilized in certain selected modes of measurement and analysis, while other programs are utilized in all modes of measurement and analysis of brain characteristic. These computer software programs are explained in the subsections described hereinbelow:

Digital Filtering

The digital filtering program is one form of an analyzer means which more particularly acts as a filter means, such as a digital filter 54 shown in FIG. 1. In selected areas of biological science the concept of digital filtering in a conventional method for removing of attenuating unwanted signals (see, for example, A. R. Moller, "Improving Brain Stem Auditory Evoked Potential Recordings by Digital Filtering,: Ear and Haring 2, 108–113 (1983); and A. V. Oppenheim et al, *Digital Signal Processing*, chap 5, Prentice-Hall, Englewood Cliffs, N.J. 1975; which are incorporated by reference herein). The user is able to attenuate or substantially remove unwanted extraneous signals from the input activity signals 14 by applying a digitized filter function thereto. The digitized filter function is loaded in the RAM 30 from the disk or tape 29 or from the remote computer 53. The digitized filter function is stored as attenuation (dB) in digitized form in the RAM 30 with an eight bit segment of the RAM 30 containing the attenuation value for one particular associated frequency. A complete frequency range for the digitized filter function is therefore embodied within a plurality of eight bit storage segments located in the RAM 30. More or less numbers of the segments can be utilized for more or less resolution of the frequency range. In performing the filtering operation the stored attenuation factors are applied to the stored amplitude at the associated frequencies to provide the reduced forms of the input activity signals 14.

In a conventional system a hardware based filter is usually applied before the signal 14 is digitized. Thus, the hardware filter is normally positioned immediately after the input activity signal 14 is output from the amplifier 26. However, in addition to attenuating unwanted signals, there is also some attenuation outside the optimum frequency range due to an inherent lack of a sharp cutoff in the attenuation for the hardware based filter. Further, the conventional hardware filter causes shifts in signal phase which distort the shape and position of the input activity signals 14. The digital filter 54 is however programmable to have a sharp cutoff and not introduce signal phase shifts when applied to the input activity signal 14. Nevertheless, where appropriate filter characteristics are achievable, the hardware filter could be utilized.

The apparatus 10 can use the digital filter 54 derived from computer system hardware and software of the apparatus 10. Digital filtering is provided by the digital filter 54 responsive to the input activity signal 14 for locations after the accumulated averaged signal 14 for locations after the accumulated averaged form of the signal 14 has been stored in the RAM 30, but before the interpolation has been performed. The digital filter 54 can be applied immediately after the input activity signal 14 is output from the multiplexer 24 (see FIG. 1) or after output from the A/D converter 28. Alternatively, the digital filter 54 is applied after the interpolated from of the input activity signal 14 has been generated.

In the illustrated embodiment, the digital filter 54 is applied after storage of the input activity signals 14 in the RAM 30. The original measured form of the input activity signal 14 is retained in unchanged form in the RAM 30; and therefore, the digital filter 54 can be changed and applied repeatedly to the input activity signal 14 in the process of the user analyzing the signal 14. The digital filter 54 is readily modified by user programming, and consequently the user has great versatility in constructing virtually any combination of low or high pass or band pass filter necessary to analyze the input activity signal 14.

Noise Evaluation

The evaluation of a noise signal often enables the user to compensate for the noise by utilizing an electronic filter, such as the digital filter 54, to attenuate the noise signal as the digital filter 54, to attenuate the noise signal to provide a reduced, or substantially noise-free, form of the input activity signal 14 for more meaningful data analysis. Alternatively, if the user can identify the source of the noise signal, the noise source might be eliminated altogether. Noise identification and attenuation or reduction is known in selected areas of biological science (see, for example, *Introduction to Automated Arrhythmia Detection*, ch. 5 K. L. Ripley and A. Murray, IEEE Computer Society, No. EH 0171.9, 1980; and see R. H. Wong and R. G. Bickford, "Brainstem Auditory Evoked Potentials: The Use of Noise Estimates," Electroencephelography 50, 25034, (1980); which are incorporated by reference herein).

Another aspect of the analyzer means is noise evaluation alone which is carried directed to determination of the noise signals. Knowing the noise signal behavior, the user can often program the digital filter 54 to attenuate the noise signal. One type of noise evaluation program is directed to evaluation of noise signals which do not have long term, constant frequency and amplitude. This type of noise evaluation is directed to, for example, noise signals comprising random noise, spurious occasional components if irregular frequency and varying aplitude and spurious temporary components of regular frequency noise.

FIG. 6 illustrates the isolation of extraneous noise signals present in the measurement of brain electrical activity signals. The converted input activity signal 14 output from the A/D converter 28 is input to multiplexer means, such as a multiplexer 56, which distributes and accumulates thew activity signal 14 in at least two alternate memory locations, a first memory 57 and a second memory 58. The signal 14 is entered into these locations by alternating data entry between the memory locations 57 and 58. If the noise signal is random noise or is a continuous but irregular frequency signal. the noise signal is characterizable by applying subtraction means to generate a subtracted output of the arithmetic difference between the input activity signals 14 in the first memory location 57 and the input activity signals 14 in the second memory location 58. Knowing the noise signal, the user can selectively attenuate this unwanted noise signal using filters, such as the digital filter 54. If, however, the noise signal happens to be similar in frequency to the input activity signal 14, the filtration is more difficult. In such cases the user might have to eliminate the source of the noise signal or alter experimental conditions to distinguish and attenuate the noise signal.

The nature of the noise signal to be evaluated also affects the analysis procedure, such as the number of values of the signal 14 to be entered in each of the memory locations 57 or 58 before switching data entry to the other memory locations 57 or 58. For evaluating random noise signals, it is acceptable to enter every odd numbered data signal in the first memory location 57 and every even numbered data signal in the second memory location 58. For example, when measuring EP response curves, every other set of values which constitute the EP response to the stimulus 16 is accumulated in the first memory location 57 and the other sets of responses are accumulated in the location 58.

When the noise spectrum takes other forms, such as spurious noise burst of irregular frequency and amplitude, correct analysis of the noise signal depends on having a substantial portion of the noise signal isolated within one segment (or other identifiable portion of one of the memory locations 57 or 58. If the noise signal is evenly distributed in the memory locations 56 and 58, this method does not enable one to readily distinguish the noise and accumulated in one of a plurality for accumulating data in each of the memory locations before switching to another of the memory locations. For example, ten entries of the signal 14 can be stored in one of a plurality of memory locations before switching to the next memory location for the next ten entries of the signal 14. Accordingly, the user should determine by independent analysis the expected varieties of noise and select the number of data entries and time period for accumulation in each of the memory locations. In this manner, noise signal which have a particular time duration can be isolated. After determination of the noise signal 14, the user can also evaluate the noise signal by calculation of a signal to noise ratio which assists in evaluating the nature to noise ratio which assists in evaluating the nature and magnitude the noise signal and provides a way to evaluate the quality of the experimental conditions.

The apparatus 10, responsive to analyzer means in the form of a software program, can evaluate the noise signal by performing a Fourier transformation to isolate the frequency components associated with the noise signal. The Fourier transformation is preferably carried out as a fast Fourier transformation procedure in a conventional manner as indicated hereinafter. Once the noise signal has been evaluated, the digital filter 54 is programmed to attenuate the known noise signal. This Fourier transformation analysis can also be preceded or followed by one of the previously discussed procedures for analyzing the noise signals.

Statistical Analysis

Statistical evaluation of an individual patient's characteristic topographical map of brain electrical activity is accomplished by such conventional approaches as z-statistics and t-statistics (see, for example, U.S Pat. Nos. 4,201,224 (John) and 3,780,724 (John) which are incorporated by reference herein). For example, in the case of z-statistics, the patient response in terms of the input activity signals 14 at each of the points of the topographical map 44 is expressed in terms of the number of standard deviations from the average response of a group of a representative normal population.

Fourier Transformation

The apparatus 10 responsive to a software program can carry out a Fourier transformation analysis of the frequency energy components in an EEG measurement. As mentioned hereinbefore, a conventional fast Fourier transformation (FFT) is preferably used to carry out the transformation of the signals 14. The FFT is explained by Oppenheim et al., *Digital Signal Processing*, ch. 6, Prentice-Hall, Englewood Cliffs, N.J., 1975, which is incorporated by reference herein.

The EEG input activity signals 14 are sampled at predetermined time intervals, approximately 2.5 second segments, to provide a selectable total number of 256 to 2048 segments of the sampled form of the EEG input activity signals 14 (see, for example, Ueno et al., "Topographic Computer Display of Abnormal EEG Activities in Patients with CNS Diseases," Memoirs of the Faculty of Engineering, Dyushu University, Volume 34, Feb., 1975, pages 195-209 which is incorporated by reference herein). In the illustrated embodiment sampling means for obtaining the signal samples takes the form of a software program in the disk 29 and is executed by the microcomputer unit 22. The software program actuates measurement of the signals 14 at the predetermined time intervals in accordance with a timing routine. The output from the Fourier transformation analysis of the segments of the input activity signal 14 enables determination of the frequency band energy output present in at least the major EEG frequency bands of $\alpha$, $\beta$, $\delta$ and $\theta$. In another form of the invention other subintervals of some of these bands are also evaluated. The frequency band energy outputs can be further analyzed by one of the statistical analysis software programs and/or the noise evaluation programs. The frequency band energy outputs are then processed by the DPU 39, and the video display 43 generates the appropriate topographical map 44.

Threshold Activation

In some modes of data acquisition, it is desirable not to enable, or actuate, accumulation and analysis of data unless the incoming input activity signals 14 attain or exceed a predetermined condition, such as a predetermined threshold amplitude or frequency level. This approach allows particular classes of data to be analyzed without superfluous data being present. For example, epileptic spikes occur intermittently and generate a large amplitude spike.

After a preliminary screening of the patient, threshold activation program data in the form of the predetermined condition is established and is placed by the input means (such as the keyboard 23 or the disk 29) into the RAM 30 or into separate hardware means for storing and testing the predetermined condition such as threshold test circuitry 55 shown in FIG. 1. The microcomputer unit 22 uses the predetermined condition stored in the RAM 30, or embodied within the circuitry 55, to compare with the incoming input activity signals 14. Therefore, the input activity signals 14 are stores and analyzed by the apparatus 10 only if the signal amplitude achieves or exceeds the predetermined condition.

The apparatus 10, responsive to a software program, can carry out a differentiation of the incoming input activity signal 14, and when the amplitude or the differentiated signal exceeds the predetermined condition, the apparatus 10 accumulates and analyzes the signal 14. In this manner the onset of a sharp spike, such as an epileptic spike having a rapidly changing curve slope, is detected, and the spike subsequently undergoes analysis.

The apparatus 10, responsive to the threshold activation program data, can detect and analyze a predetermined threshold frequency level by employing frequency means in the form of conventional frequency counting circuitry (see, for example, "Electronics for Scientists and Engineers", Prentice Hall, Englewood Cliffs, New Jersey, 1967, pages 321-322 and 470-473, which is incorporated by reference herein). The output from the frequency counting circuit is a signal whose amplitude is proportional to the frequency detected therefore, the predetermined condition for the threshold frequency level is set to actuate data acquisition and analysis of the incoming input activity signal 14 whenever the predetermined frequency level has been exceeded.

The apparatus 10 can also measure the number of zero crossing events (a form of frequency determination) and data taking is activated upon exceeding a predetermined number of such events. The microcomputer unit 22 or the test circuitry 55 evaluates the algebraic sign for each one of the input activity signals 14 and maintains a running count of the number of changes in the algebraic sign within a given time period. When the number of algebraic sign changes within the given time period exceeds a predetermined number, data accumulation and analysis is activated, and the resulting input activity signals 14 are displayed as the topographical maps 44.

The apparatus 10 responsive to the threshold activation program is able to actuate analysis of any of the input activity signals 14 wherein the user wishes to restrict analysis, for example, to a large amplitude signal, to a high frequency signal or to other selected distinguishable features. Advantages of the threshold activation program include use of less overall storage area in memory for analysis of the signals 14, performance of more detailed data analysis in a given time period of actual calculation by the microcomputer and faster and more efficient analysis of a complete data set compared to the case of analyzing all incoming data.

Integration, Differentiation and Difference Measurements

The apparatus 10 responsive to an integration software program can operate on frames of the input activity signals 14 measured for EP responses to characterize the time integrated response output. This integrated output enables an evaluation of spatial locations on the patient's head 13 and/or the time segments of the EP response which make the most important contributions to the input activity signals 14. Integration is carried out over a range of user selected time segments, and in FIG.

7 the integrated output for some of the selectable time segments is displayed in the resulting topographical maps 44. The integrated output of the input activity signals 14 of the topographical maps 44 results in combining a number of separate smaller time period segments of the input activity signals 14. Therefore, the user views in a small number of the topographical maps 44 the behavior of the input activity signals 14 over a broad time range. The time range of 0 to 240 milliseconds is shown in only six frames of integrated EP response. Such a display mode is therefore beneficial to the user to carry on an evaluation of a large amount of data without requiring separate display of a large number of the topographical maps 44 and without having to switch between a large number of the topographical maps 44.

The apparatus 10, responsive to a differentiation software program, operates on frames of the input activity signals 14 from EP responses to characterize the first or second order differential of the EP responses. This differential response enables an evaluation of locations of the time segments which contain the most significant contributions to changes (first order) and rate of change (second order) in the amplitude with respect to location and time of the EP response curves. The user can select the spatial location and/or the time interval over which the differentiation is calculated. The analysis enables spatial and time analysis of rapidly changing EP responses which supplements information obtained from the integration output. The analysis can also be carried out for changes and rate of change in amplitude with respect to location for the EEG input activity signals 14.

The apparatus 10 is also responsive to a difference software program which operates on frames of the input activity signals 14 from the EP responses to evaluate the arithmetic difference from one of the user selected frames to another, each of the frames characteristic of a preselected time after application of the stimulus 16.

Montage Analysis

The apparatus 10 responsive to a computer montage analysis program, can carry out a difference type of analysis of the input activity signals 14 to isolate and identify features of interest, such as epileptic spikes. The analysis is accomplished by selecting one of more of the electrode sensors 12 as reference electrodes with the rest of the electrode sensors 12 having the roles of active electrode sensors 12. The montage analysis is performed by using the input activity signals 14 stored in memory means, such as the RAM 30, and thus repeated actual measurements are unnecessary. The twenty-one electrode sensors in FIG. 1 are assigned active roles and an additional electrode sensor 12 is attached near the patient's ear to act as the reference electrode sensor 12. The difference form of the input activity signal 14 is calculated, and the values are stored in the RAM 30. The user then views the difference signals 14 and determines the approximate location of the feature of interest. The user next selects new ones of the reference electrode sensors 12 and active electrode sensors 12 which are in close proximity to the feature of interest. The difference form of the input activity signals 14 are calculated, and the location and appearance of the feature of interest is isolated with greater precision. This interaction continues by recycling back to the selection of new ones of the reference and active electrode sensors 12 until completion of the identification of the feature of interest.

For each selected set of the reference and active electrode sensors 12, an average value can be calculated for each set of the sensors 12 in every frame of the input activity signals 14. These average values are then subtracted from one another to form the difference form of the signals 14. For example, if the feature of interest is a sharp peak extending along a line, the user could select ten of the sensors on one side of the distended peak as reference electrodes and eleven on the other side as active electrodes. The average of each set is then subtracted from the average of the other for each of the frames. The difference form of the input activity signals 14 is then calculated for a selected number of the frames, (for example, the user can select from the 240 frames of the measured EP response taken every four milliseconds from 0 to 960 milliseconds after the application of the stimulus 16. As discussed hereinabove, this interactive analysis procedure can be repeated using recycles means to return to the beginning of the montage interactive analysis procedure by selecting a different set of the electrode sensor 12. This iterative process is continued until the source of any feature of interest, such as the above mentioned distended type of peak, is identified or isolated. This procedure can be programmed to iterate automatically to a solution, or the user can interact to select various combinations of active and reference electrode sensors 12 to locate the most prominent features. Therefore, the recycle means can be a user signal to return to perform another interactive analysis or can be an interrupt and branching command in the software program to automatically recycle until the specified feature is identified in accordance with predetermined conditions stored in the RAM 30. The resulting set of difference input activity signals are stored in the RAM 30 at locations different from the input activity signals 14 and are compared to one another. These difference input activity signals 14 can also undergo the additional analysis 40 and provide other forms of the topographical maps 44 of EP response and EEG measurements. Display of the difference signals 14 and their derivatives from the analysis 40 enable diagnosis of disparities associated with brain abnormalities.

Montage analysis has important advantages over the prior art because the instant approach uses only one set of the measured input activity signals 14 which are stored in the RAM 30. Conventional methods, however, require repeated measurements since the montage analysis proceeds by selecting a first set of one or more reference electrode sensors 12, measuring a set of signals for the remainder of the plurality of the electrode sensors 12, computing and recording the difference of the signals 14, establishing a new set of reference electrode sensors 12 and measuring a new set of differences in the signals 14. This procedure is sequentially repeated until the location of the feature of interest has been isolated. The computer program montage analysis renders unnecessary this time consuming and repetitive task and substantially reduces the time for data taking and analysis.

Cognitive Test Mode

The apparatus 10 responsive to a cognitive testing software program effectuates EP response tests of recognition ability which enables diagnosis of a number of abnormalities (see, for example, U.S. Pat. No. 3,901,215 (John) which is incorporated by reference herein). The instant cognitive testing program makes full use of one time period of data acquisition by sorting the responses to a predetermined pattern of mixed or different types of the stimuli 16 into different memory locations of the RAM 30. Ordinarily cognitive testing is accomplished by acquiring the input activity signals 14 for a plurality of completely different time periods, wherein each time period is devoted solely to either a regular form of the stimulus 16 and response thereto or to an intermittent form of the stimulus 16 and associated response. Examples of the different types of the stimuli 16 can include a mixture of different amplitude audible tones, tones of different frequency and a tone pattern with intermittent absences of certain anticipated tones.

The microcomputer unit 22 controls administration of he predetermined pattern of the stimulus 16 during the cognitive testing mode of operation responsive to the cognitive test software, and therefore the microcomputer unit 22 flags each of the applied stimuli 16 and depending on the nature of the stimulus 16 the flagging enables the microcomputer 22 to sort the resulting EP responses comprised of a set of the input activity signals 14 associated with each type of the stimulus 16, into the different respective memory locations. Comparison and analysis, such as statistical analysis, is then performed on the signals 14 sorted in the different memory locations. This procedure therefore makes data collection more efficient and reduces the time to collect sufficient data characteristic of the input activity signals 14.

Video display and Interaction Modes

The apparatus 10 responsive to an interface software program results in the interpolation and the output to the display memory of the DPU 39 of every other pixel line in one frame to the video display 43. Upon completion of display of every other pixel line in a first complete frame, or first topographical map 44, the program causes return of the raster beam to the beginning of the display cycle to perform alternate pixel line interpolation and display in the next frame, or the next topographical map 44, or the set of pixel lines skipped in the first display cycle. By virtue of having to process and display only every other pixel line of the input activity signals 14, the interlace mode enables an apparent increase in display speed by updating at, for example, twelve frames/second the display memory of the DPU 39. The video display 43 therefore generates a plurality of the topographical maps 44 at an apparent rate of nearly twenty-four frames/second because in each frame every other pixel line is displayed. This results in a smooth cartooning effect without apparent loss of resolution to the human eye.

In the interaction modes the mouse 36 or the light pen 34 are preferably used as indicator means. The user generates an input signal so as to interact with the information present on the video display 43 thereby actuating selected software programs. In the case of the mouse 34, this use takes the form of displaying a variety of selectable routines on the video display 43, moving a cursor to pint to a designated label for one of the routines and carrying out the routine by actuating a switch (not shown) on the mouse 36. Similarly, for the light pen 34, the user points to a location on the video display 43, and a screen sensor (not shown) detects the site of the light pen light spot and generates an activation output to the microcomputer unit 22 to actuate the appropriate software program. The software program also displays additional information relevant to the displayed topographical map 44, or further calculations can be performed and displayed. For example, the user is able to selectively display the evoked potential waveforms 50 (illustrated in FIG. 5) for those points on the topographical map 44 designated by the mouse 34 or by the light pen 34.

The apparatus 10, responsive to an interaction means in the form of a software program, can also generate the amplitude of input activity signal contours along any indicated line on the topographical map 44, the line being selected by the cursor of the mouse 36 or by the light pen 34. Further, the software program can act as a map magnifying means by allowing the user to utilize the mouse 36 or the light pen 34 to select an outline of an area of the topographical map 44 and expand the delineated portion to fill a selected portion of the video display 43.

While preferred embodiments of the present invention have been illustrated and described, it will be understood that changes and modifications can be made without departing from the invention in the broader aspects. Various features of the invention are set forth in the following claims.

What is claimed:

1. A method of evaluating brain functionality of a subject comprising the steps of:
   providing neuropsychological test result data obtained from said subject in response to at least one preselected test;
   generating a weighted matrix of test output signals by applying to said test result data a plurality of coefficients, each said coefficient being representative of said one preselected test and corresponding to a preselected region of the brain; and
   displaying said weighted matrix of test output signals as a topographic map.

2. The evaluation method of claim 1 wherein said test result data is provided for a plurality of preselected tests.

3. The evaluation method of claim 1 wherein said test result data comprises a normatively based statistical analysis of test results obtained from said subject.

4. The evaluation method of claim 1 wherein said test result data is provided for a plurality of tests; said coefficients are applied to said test result data for each said test to obtain a plurality of test output signal matrices; and said plurality of test output signal matrices are combined to obtain a composite test output signal matrix which is displayed as a topographic map.

5. The evaluation method of claim 4 wherein said test result data comprises a normatively based statistical analysis of test results obtained from said subject.

6. The evaluation method of claim 1 further including the steps of measuring at least one predetermined physical parameter of the subject's brain, generating a matrix of physical output signals in response to said measured parameter, and simultaneously displaying a topographic map of said physical output signals with said topographic map of said test output signals.

7. The evaluation method of claim 6 wherein said measuring step comprises an electroencephalogram measurement.

8. The evaluation method of claim 6 wherein said measuring step comprises an evoked potential measurement.

9. The evaluation method of claim 6 wherein said measuring step comprises a magnetoencephalogram measurement.

10. The evaluation method of claim 6 wherein said measuring step comprises positron emission tomography.

11. The evaluation method of claim 6 wherein said measuring step comprises cerebral blood flow measurement.

12. The evaluation method of claim 1 further including the steps of measuring at least one physical parameter of the subject's brain, generating a matrix of physical output signals responsive to said measured parameter, and combining said test output signal matrix with said physical output signal matrix to obtain a composite output signal matrix which is displayed as a topographic map.

13. The evaluation method of claim 1 wherein said topographic map depicts brain functionality at an internal surface or plane within the subject's brain.

14. The evaluation method of claim 1 wherein said topographic map is displayed within a three-dimensional representation of the human head.

15. The evaluation method of claim 14 wherein said topographic map and three-dimensional representation are changed to provide a different perspective view.

16. The evaluation method of claim 1 further including the steps of generating interpolated output signals between adjacent test output signals and displaying said interpolated and test output signals together as a topographic map.

17. The evaluation method of claim 1 further including the steps of measuring at least one physical parameter of the subject's brain, generating a display of said one physical parameter and superimposing said physical parameter display over the display of said topographic map.

18. The evaluation method of claim 17 wherein said topographic map and superimposed physical parameter display are presented within a three-dimensional representation of the human head.

19. The evaluation method of claim 17 wherein said measuring step comprises an electroencephalogram measurement.

20. The evaluation method of claim 17 wherein said measuring step comprises an evoked potential measurement.

21. The evaluation method of claim 17 wherein said measuring step comprises a magnetoencephalogram measurement.

22. The evaluation method of claim 17 wherein said measuring step comprises positron emission tomography.

23. The evaluation method of claim 17 wherein said measuring step comprises cerebral blood flow measurement.

24. The evaluation method of claim 1 further including the steps of scanning the anatomy of the subject's brain, generating a display of said anatomy and superimposing said anatomical display over the display of said topographic map.

25. The evaluation method of claim 24 wherein said topographic map and said anatomical display are presented within a three-dimensional representation of the human head.

26. The evaluation method of claim 24 wherein said anatomical display is made by x-ray computerized tomography.

27. The evaluation method of claim 24 wherein said anatomical display is made by nuclear magnetic resonance imaging.

28. The evaluation method of claim 1 further including the steps of scanning the anatomy of the subject's brain, generating a matrix of anatomical output signals, and simultaneously displaying an image of said anatomical output signals with said topographic map of said test output signals.

29. The evaluation method of claim 28 wherein said topographic map and said anatomical display are presented within a three-dimensional representation of the human head.

30. The evaluation method of claim 28 wherein said anatomical display is made by x-ray computerized tomography.

31. The evaluation method of claim 28 wherein said anatomical display is made by nuclear magnetic resonance imaging.

32. A method of evaluating brain-functionality of a subject comprising the steps of:
providing neuropsychological test result data obtained from said subject in response to at least one preselected test;
generating a matrix of test output signals by applying to said test result data a plurality of coefficients, each said coefficient being representative of said one preselected test and corresponding to a preselected region of the brain;
generating interpolated output signals between adjacent test output signals; and
displaying said test output signals and said interpolated output signals as a topographic map.

33. The evaluation method of claim 32 wherein said test result data is provided for a plurality of preselected tests.

34. The evaluation method of claim 32 wherein said test result data comprises a normatively based statistical analysis of test results obtained from said subject.

35. The evaluation method of claim 32 wherein said test result data is provided for a plurality of tests; said coefficients are applied to said test result data for each said test to obtain a plurality of test output signal matrices; and said plurality of test output signal matrices are combined to obtain a composite test output signal matrix which is displayed with said interpolated output signals as a topographic map.

36. The evaluation method of claim 32 further including the steps of measuring at least one predetermined physical parameter of the subject's brain, generating a matrix of physical output signals in response to said measured parameter, and simultaneously displaying a topographic map of said physical output signals with said topographic map of said test output signals.

37. The evaluation method of claim 32 further including the steps of measuring at least one physical parameter of the subject's brain, generating a matrix of physical output signals responsive to said measured parameter, and combining said test output signal matrix with said physical output signal matrix to obtain a composite output signal matrix which is displayed as a topographic map.

38. The evaluation method of claim 32 wherein said topographic map depicts brain functionality at an internal surface or plane within the subject's brain.

39. The evaluation method of claim 32 wherein said topographic map is displayed within a three-dimensional representation of the human head.

40. The evaluation method of claim 32 further including the steps of measuring at least one physical parameter of the subject's brain, generating a display of said one physical parameter and superimposing said physical parameter display over the display of said topographic map.

41. The evaluation method of claim 32 further including the steps of scanning the anatomy of the subject's brain, generating a display of said anatomy and superimposing said anatomical display over the display of said topographic map.

42. A method of evaluating brain functionality of a subject comprising the steps of:
providing neuropsychological test result data obtained from said subject in response to at least one preselected test;
generating a plurality of test output signals from said test result data, each said test output signal corresponding to said one preselected test and a preselected region of the brain; and
displaying said plurality of test output signals as a topographic map.

43. A method of evaluating brain functionality of a subject comprising the steps of:
providing neuropsychological test result data obtained from said subject in response to at least one preselected test;
generating a matrix of weighted test output signals from said test result data, each said weighted output signal being representative of said one preselected test and a preselected region of the brain; and
displaying said matrix of weighted test output signals as a topographic map.

* * * * *